(12) United States Patent
Van Houten et al.

(10) Patent No.: US 11,324,223 B2
(45) Date of Patent: May 10, 2022

(54) SYSTEM FOR RELEASING BENEFICIAL MITES AND USES THEREOF

(71) Applicant: Koppert B.V., Berkel en Rodenrijs (NL)

(72) Inventors: Yvonne Maria Van Houten, Berkel en Rodenrijs (NL); Arend Veenman, Berkel en Rodenrijs (NL); Hans Hoogerbrugge, Berkel en Rodenrijs (NL); Nicholas George Petrus Beveridge, Berkel en Rodenrijs (NL); Thomas Volkert Marie Groot, Berkel en Rodenrijs (NL)

(73) Assignee: Koppert B.V., Berkel en Rodenrijs (NL)

( * ) Notice: Subject to any disclaimer, the term of this patent is extended or adjusted under 35 U.S.C. 154(b) by 67 days.

(21) Appl. No.: 16/630,993

(22) PCT Filed: Jul. 16, 2018

(86) PCT No.: PCT/NL2018/050490
§ 371 (c)(1),
(2) Date: Jan. 14, 2020

(87) PCT Pub. No.: WO2019/017776
PCT Pub. Date: Jan. 24, 2019

(65) Prior Publication Data
US 2020/0221706 A1    Jul. 16, 2020

(30) Foreign Application Priority Data

Jul. 16, 2017 (EP) .................................. 17075012
Jul. 17, 2017 (NL) .................................. 2019261

(51) Int. Cl.
*B32B 27/10* (2006.01)
*A01N 63/14* (2020.01)
(Continued)

(52) U.S. Cl.
CPC ............ *A01N 63/14* (2020.01); *A01K 67/033* (2013.01); *B32B 27/32* (2013.01);
(Continued)

(58) Field of Classification Search
CPC ........ A01N 25/34; A01N 63/16; A01N 63/14; A01K 2227/706; A01K 67/033;
(Continued)

(56) References Cited

U.S. PATENT DOCUMENTS 3,738,566 A    6/1973 Foster
2005/0178337 A1    8/2005 Wright

FOREIGN PATENT DOCUMENTS

GB    531965 A    1/1941
WO    WO2010079353 A1    7/2010
WO    WO2017123094 A1    7/2017

OTHER PUBLICATIONS

Tetra Pak, Development in Brief, Published May 14, 2013, Retrieved May 20, 2015, from URL: http://www.tetrapak.com/DocumentBank/9704en.pdf, p. 1-86.

*Primary Examiner* — Lawrence D Ferguson
(74) *Attorney, Agent, or Firm* — Mandar A. Joshi; Bret E. Field; Bozicevic, Field & Francis LLP

(57) ABSTRACT

This invention relates to an improved system for releasing beneficial mites and the use of such a system. Mite species that can be used beneficially for human purposes may for example be employed in the control of pests, such as in the field of agriculture, including agricultural production systems for plant products, agricultural production systems for animal products, and animal husbandry, or in the field of storage of food products. The system of the invention may find use in any of these fields.

16 Claims, 10 Drawing Sheets

(51) Int. Cl.
*A01K 67/033* (2006.01)
*B32B 27/32* (2006.01)
*B32B 9/06* (2006.01)
*B32B 27/12* (2006.01)

(52) U.S. Cl.
CPC .......... *A01K 2227/706* (2013.01); *B32B 9/06* (2013.01); *B32B 27/10* (2013.01); *B32B 27/12* (2013.01); *B32B 2250/03* (2013.01); *B32B 2255/205* (2013.01); *B32B 2255/26* (2013.01); *B32B 2307/724* (2013.01); *B32B 2307/728* (2013.01); *B32B 2307/7246* (2013.01); *B32B 2307/73* (2013.01); *B32B 2410/00* (2013.01)

(58) Field of Classification Search
CPC ............ B32B 2250/02; B32B 2250/03; B32B 2255/10; B32B 2255/12; B32B 2255/205; B32B 2255/26; B32B 2262/06; B32B 2262/062; B32B 2307/30; B32B 2307/41; B32B 2307/412; B32B 2307/50; B32B 2307/54; B32B 2307/7163; B32B 2307/718; B32B 2307/724; B32B 2307/7244; B32B 2307/7246; B32B 2307/726; B32B 2307/728; B32B 2307/73; B32B 2307/732; B32B 2410/00; B32B 2439/06; B32B 2439/46; B32B 27/08; B32B 27/10; B32B 27/12; B32B 27/16; B32B 27/32; B32B 3/26; B32B 7/08; B32B 9/02; B32B 9/06

See application file for complete search history.

| | standaardvoedingsoplossing (mmol/l) | | | | | | | | |
|---|---|---|---|---|---|---|---|---|---|
| | NO3- | H2PO4- | SO4 2- | NH4+ | K+ | Ca+ | Mg 2+ | H3O+ | OH- |
| Basis/standaard | 16,15 | 1,25 | 1 | 1,25 | 6,5 | 4,75 | 1 | | |
| Correcties | | | | | | | | | |
| Na correcties | | | | | | | | | |
| mol voor 1000 liter | 1615 | 125 | 100 | 125 | 650 | 475 | 100 | | |
| KNO3 | 525 | | | | 525 | | | | |
| KH2PO4 | | 125 | | | 125 | | | | |
| MgSO4 | | | 100 | | | | 100 | | |
| Ca(NO3)2 | 1045 | | | 80 | | 475 | | | |
| NH4NO3 | 45 | | | 45 | | | | | |
| Mg(NO3)2 | | | | | | | | | |
| H3PO4 | | | | | | | | | |
| K2SO4 | | | | | | | | | |
| HNO3 | | | | | | | | | |
| KOH | | | | | | | | | |
| | 1615 | 125 | 100 | 125 | 650 | 475 | 100 | 0 | 0 | 0 |
| | 0 | 0 | 0 | 0 | 0 | 0 | 0 | 0 | 0 | 0 | pH = 5.5, EC = 2.0

Top before wipe: (B) 34g/m² BUI foil, (A) 34g/m² BUI foil with TiO2
Bottom after wipe: (B) 34g/m² BUI foil, (A) 34g/m² BUI foil with TiO2

34g/m² BUI foil + 40g/m² kraft paper, left before wipe, right after wipe.

microscope slide glass, left before wipe, right after wipe.

Ref. nr. 1214, left before wipe, right after wipe.

SYSTEM FOR RELEASING BENEFICIAL MITES AND USES THEREOF

FIELD OF THE INVENTION

This invention in general relates to the use of mite species for human purposes. Mite species that can be used beneficially for human purposes may for example be employed to control pests, such as in the field of agriculture, including agricultural production systems for plant products, agricultural production systems for animal products, and animal husbandry, in the field of storage of food products. In such uses, predatory mite species as well as mite species suitable as prey for predatory mite species or for other predatory arthropod species may be considered beneficial.

BACKGROUND

Within agriculture, including horticulture, the use of beneficial mites is known. For example predatory mites, such as those described in EP1686849B1, EP2042036B1, EP1830631B1, EP1965634B1 may be employed to control crop pests. EP2405741 and EP2612551B1 mention a further number of beneficial predatory mites. The areas mentioned above where mite species may be employed for human benefit encompass/include only a few of the possibilities.

For successfully employing beneficial mites, the successful release of the beneficial mites in a target area is required. Various systems have been developed to release beneficial mites or to provision them with prey mites. In the traditional systems, beneficial mites are placed either in containers made of materials that are permeable for metabolic gasses (in particular $O_2$) or that have relatively large ventilation openings as to allow gas exchange with the ambient atmosphere. This on the basis of the general conviction in the art, that the prolonged survival (during at least 2 weeks) of beneficial mites in the containers requires extensive gas exchange. These requirements are amongst others reflected by GB2393890 (see e.g. page 4, line 30-page 5, line 2) relating to a releasing system for beneficial insects and mites made of materials permeable to gas (fabric or polyethene (PE) coated paper).

However, for the prolonged release of beneficial mites, the use of systems that employ materials that are permeable for gasses and/or that have relatively large ventilation openings have certain drawbacks. In particular materials that are considerably permeable to gases also allow considerable exchange of water vapour. Similarly, large ventilation openings apart from allowing exchange of metabolic gasses also allow water vapour outflow. In addition large ventilation openings impose a risk of liquid water entering the interior of the system, where the beneficial mites are present. Due to this, maintaining moisture levels within targeted ranges is a problem with the prior art systems. A moisture level outside targeted ranges may have undesired effects on the health and/or population development of the beneficial mites in the systems. Due to this, for prolonged functioning the traditional systems for releasing beneficial mites require an ambient relative humidity of about 70% or higher.

Recently, after careful investigations by the applicant's research team, it has surprisingly been found that contrary to the general conviction that gas permeable materials and/or relatively large ventilation openings must be used in systems for prolonged releasing (providing) beneficial mites, it is possible to effectively maintain populations of species of beneficial mites in a compartment enclosed by a material having a low gas permeability and wherein the openings, that connect the interior of the compartment (containing the mite individuals) with the exterior, are relatively small (e.g. such as within the size range of existing systems employing gas permeable materials). These findings are at the basis of the various aspects of the invention filed in non-prepublished patent applications EP17151679.2 and PCT/NL2017/050022, now published as EP3192366A1 and WO2017/123094 A1 respectively. Further research into the functioning in the field of this new generation of mite releasing systems has revealed that further improvements may be made. These further improvements are at the basis of the present invention.

Amongst others, it has been found that, under certain conditions, there is a risk of water inflow into the mite compartment when mite releasing systems are constructed from a laminate film comprising a metalized polymer film, even when these systems comprise a single mite exit with a small diameter (such as about 0.7 mm). The occurrence of this problem was surprising and is unreported. To reduce the risk of water inflow, further research was done. During which surprisingly it has been found that when using a laminate film comprising as an outer layer a paper layer, the risk of water entry was reduced. Careful analysis of the occurring problem and the solution provided by the paper layer has brought the inventors to the conclusion that the risk of water inflow is reduced by using on the outer surface of the mite releasing system a water film maintaining material.

SUMMARY

The invention therefore according to a first aspect relates to a system for releasing beneficial mites consisting of a compartment, the "mite compartment", holding a population of a beneficial mites species, preferably in association with a carrier, and a food source for the beneficial mites wherein said mite compartment is enclosed by an enclosing material having an inner surface bordering the mite compartment, an outer surface at the exterior of the mite compartment and comprising a gas barrier material, having a water vapour transmission rate of $\leq 5$ g/m$^2$*24 hours, said mite compartment having a volume x of between $3*10^3$ to $600*10^3$ mm$^3$ and wherein the system further comprises a number of connections that connect the mite compartment with the space outside the mite compartment, said number of connections each having an area y of between 0.1 and 4.0 mm$^2$, wherein the sum of the areas of the number of connections is $\Sigma y$ and wherein $5*10^3$ mm$\leq x/\Sigma y \leq 70*10^3$ mm, preferably $6*10$ mm$\leq x/\Sigma y \leq 60*10^3$ mm, more preferably $7*10^3$ mm$\leq x/\Sigma y \leq 50*10^3$ mm. The system for releasing beneficial mites is characterized in that the outer surface of the enclosing material comprises a water film maintaining material.

A further aspect of the invention relates to the use of the system according to the invention for introducing a beneficial mite species in a target area and a method for controlling in a target area a pest capable of being preyed by a predatory arthropod species said method comprising, providing the system according to the invention to said target area.

Yet another aspect of the invention relates to a method for producing an agricultural product from a number of non-human organisms susceptible to a pest capable of being preyed by a predatory arthropod species, said method comprising:

providing the number of non-human organisms in an area, the target area;

providing in the target area a number of systems according to the invention;

providing to the number of non-human organisms suitable nutrients and environmental conditions to produce the agricultural product.

A further aspect of the invention relates to a laminate comprising a metalized polymer film having a water vapour transmission rate of ≤5 g/m²*24 hours, and an outer layer of a water absorbing porous material, such as paper.

According to a further aspect the invention relates to the use of the laminate of the invention as a construction material for a system for releasing beneficial mites comprising a mite compartment for holding the beneficial mites, such as a sachet.

The invention also relates to a method for producing a system for releasing beneficial mites wherein the laminate of the invention is used as a construction material.

DETAILED DESCRIPTION

Figure 1:
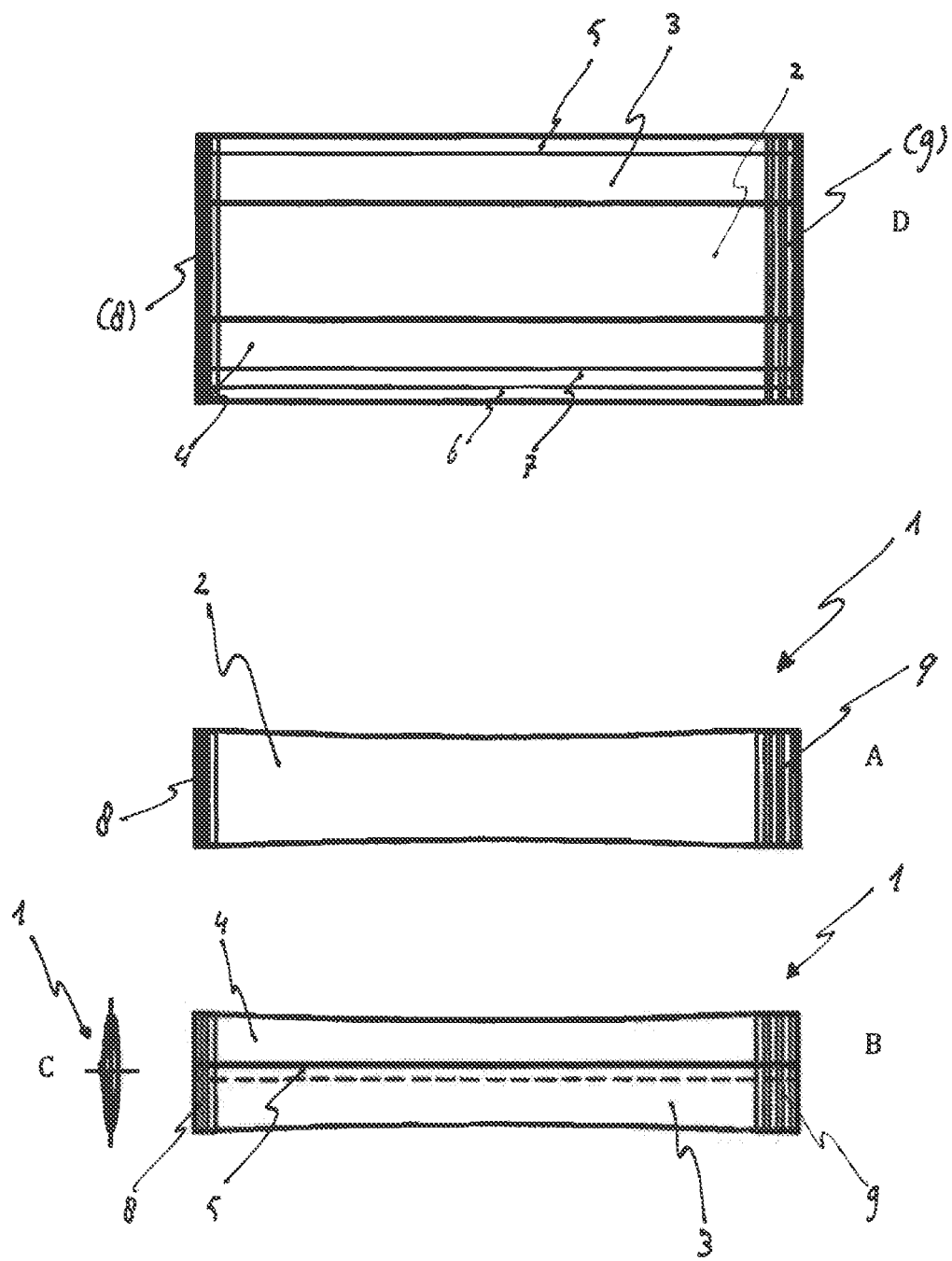
FIG. 1A presents a view on the front side of a mite releasing system according to the invention.
FIG. 1B presents a view on the rear side of a mite releasing system according to the invention.
FIG. 1C presents a view in the direction of the longest axis of the mite releasing system presented in FIGS. 1A and 1B.
FIG. 1D presents a planar foil from which the mite rearing system of figures IA-IC is formed.

The system of the invention is a system suitable for releasing beneficial mites. The system comprises structural elements, in particular an enclosing material, and in certain embodiments also others, and biological elements, in particular the population of beneficial mites. Such a system for releasing beneficial mites may also be referred to as a device for releasing beneficial mites or a container for releasing beneficial mites. The term "system" thus may be substituted with any of the terms "device" or "container".

The biological terms "mite" and "mites" will be clear to the skilled person. In particular the skilled person will know that mites are invertebrate animals from the subclass Acari characterised by having an exoskeleton and jointed appendages. The beneficial mites to be released by the system of the invention are beneficial in respect of useful functions they may perform. Such useful functions may for example include functions in agriculture, including horticulture, such as control of populations of insect and/or mite pests. In particular predatory mites are useful for the control of populations of insect and/or mite pests or nematodes. Alternatively the beneficial mites may be useful in the sense that they may serve as a food source for beneficial predatory mites or other beneficial predatory arthropods, while not being a pest in the target area where they are employed. In this way they may support the development of a population of a predatory species present in the target area (either by human introduction or by being naturally present) with a minimal risk of causing negative effects in the target area. As such the term "beneficial" should be understood as meaning "useful".

Predatory mites may for example be selected from:
Mesostigmatid mite species such as from:
i) Phytoseiidae such as from:
the subfamily of the Amblyseiinae, such as from the genus *Amblyseius*, e.g. *Amblyseius andersoni, Amblyseius aerialis, Amblyseius swirskii, Amblyseius herbicolus* or *Amblyseius largoensis*, from the genus *Euseius* e.g. *Euseius finlandicus, Euseius hibisci, Euseius ovalis, Euseius victoriensis, Euseius stipulatus, Euseius scutalis, Euseius tularensis, Euseius addoensis, Euseius concordis, Euseius ho, Euseius gallicus, Euseius citrifolius* or *Euseius citri*, from the genus *Iphiseiodes* e.g. *Iphiseiodes zuluagi*, from the genus *Iphiseius* e.g. *Iphiseius degenerans*, from the genus *Neoseiulus* e.g. *Neoseiulus barkeri, Neoseiulus californicus, Neoseiulus cucumrneris, Neoseiulus longispinosus, Neoseiulus wornersleyi, Neoseiulus idaeus, Neoseiulus anonymus, Neoseiulus paspalivorus, Neoseiulus reductus* or *Neoseiulus fallacis, Neoseiulus baraki* from the genus *Amblydromalus* e.g. *Amblydromalus limonicus* from the genus *Typhlodroinmalus* e.g. *Typhlodromalus aripo, Tvphlodromalus lailae* or *Typhlodromalus peregrinus* from the genus *Transeius* (alternatively known as *Typhlodromips*) e.g. *Transeius montdorensis* (alternatively known as *Typhlodromips mnontdorensis*), from the genus *Phytoseiulus*, e.g. *Phytoseiulus persimilis, Phytoseiulus macropilis, Phytoseiulus longipes, Phytoseiulus fragariae;* the subfamily of the Typhlodrominae, such as from the genus *Galendromus* e.g. *Galendromus occidentalis,* from the genus *Metaseiulus* e.g. *Metaseiulus flumenis,* from the genus *Gynaeseiu* e.g. *Gynaeseius liturivorus* from the genus *Typhlodromus* e.g. *Typhlodromus exhilarates, Typhlodromus phialatus, Typhlodromus recki, Typhlodromus transvaalensis, Typhlodromus pyri. Typhlodromus doreenae* or *Typhlodronmus athiasae;* ii) Ascidae such as from the genus *Proctolaelaps,* such as *Proctolaelaps pygmaeus* (Muller); from the genus *Blat-* tisocius e.g. *Blattisocius tarsalis* (Berlese), *Blattisocius keegani* (Fox); from the genus *Lasioseius* e.g. *Lasioseius fimetorum* Karg, *Lasioseius floridensis* Berlese, *Lasioseius bispinosus* Evans, *Lasioseius dentatus* Fox, *Lasioseius scapulatus* (Kenett), *Lasioseius athiasae* Nawar & Nasr; from the genus *Arctoseius* e.g. *Arctoseius semiscissus* (Berlese); from the genus *Protogamasellus* e.g. *Protoganiasellus dioscorus* Manson;

iii) Laelapidae such as from the genus *Stratiolaelaps* e.g. *Stratiolaelaps scinitus* (Womersley); *Gaeolaelaps* e.g. *Gaeolaelaps aculeifer* (Canestrini); *Androlaelaps* e.g. *Androlaelaps casalis* (Berlese), *Cosmolaelaps* e.g. *Cosmolaelaps claviger, Cosmolaelaps jaboticabalensis;* iv) Macrochelidae such as from the genus *Macrocheles* e.g. *Macrocheles robustulus* (Berlese), *Macrocheles muscaedomesticae* (Scopoli), *Macrocheles matrius* (Hull);

v) Parasitidae such as from the genus *Pergainasus* e.g. *Pergamasus quisquiliarum* Canestrini; *Parasitus* e.g. *Parasitus fimetorum* (Berlese), *Parasitus bituberosus, Parasitus mycophilus, Parasitus mammilatus;*

Prostigmatid mite species such as from:

vi) Tydeidae such as from the genus *Homeopronemnatus* e.g. *Homeopronematus anconai* (Baker); from the genus *Tydeus* e.g. *Tydeus lambi* (Baker), *Tydeus caudatus* (Dugés); from the genus *Pronematus* e.g. *Pronematus ubiquitous* (McGregor);

vii) Cheyletidae such as from the genus *Cheyletus* e.g. *Cheyletus eruditus* (Schrank), *Cheyletus malaccensis* Oudemans;

viii) Cunaxidae such as from the genus *Coleoscirus* e.g. *Coleoscirus simplex* (Ewing), from the genus *Cunaxa* e.g. *Cunaxa setirostris* (Hermann)

ix) Erythraeidae such as from the genus *Balaustium* e.g. *Balaustium putmani* Smiley, *Balaustium medicagoense* Meyer & Ryke, *Balaustium murorum* (Hermann), *Balaustium hernandezi, Balaustium leanderi;* x) Stigmaeidae such as from the genus *Agisteinus* e.g. *Agistemus exsertus* Gonzalez; such as from the genus *Zetzellia* e.g. *Zetzellia mali* (Ewing);

xi) Anystidae, such as from the genus *Anystis*, e.g. *Anystis baccarum*.

In view of their predatory behaviour towards important pests, predatory mites preferably are selected from the family Phytoseiidae, in particular from the genus *Amblyseius*, such as *Amblyseius swirskii, Amblyseius largoensis* and *Amblyseius andersoni*, from the genus *Neoseiulus*, such as *Neoseiulus californicus, Neoseiulus cucumeris, Neoseiulus barkeri, Neoseiulus baraki* and *Neoseiulus longispinosus* and *Neoseiulus fallacis*, in particular from the genus *Euseius*, such as *Euseius gallicus*, in from the genus *Iphiseius*, such as *Iphiseius degenerans*, from the genus *Transeius*, such as *Transeius montdorensis*, from the genus Amblydromralus, such as *Amblydromalus limonicus* (alternatively known as *Typhlodromalus* limnonicus), from the genus *Galendromus*, such as *Galendromus occidentalis*, from the genus *Phytoseiulus*, such as *Phytoseiulus persimilis, Phytoseiulus macropilis* and *Phytoseiulus longipes*, from the family Cheyletidae, in particular from the genus *Cheyletus*, such as *Cheyletus eruditus*, from the family Laelapidae, in particular from the genus *Androlaelaps*, such as *Androlaelaps casalis*, from the genus *Stratiolaelaps*, such as *Stratiolaelaps scirnitus* (Alterntively known as *Hiypoaspis miles*), from the genus *Gaeolaelaps*, such as *Gaeolaelaps aculeifer* (Alternatively known as *Hypoaspis aculeifer*), or from the family Macrochelidae, in particular from the genus *Macrocheles*, such as *Macrocheles robustulus*. From within these preferred selections of the predatory mite, the predatory mite is most preferably selected from the family Phytoseiidae.

The names of the Phytoseiidae are as referred to in Chant D. A., McMurtry, J. A. (2007) Illustrated keys and diagnoses for the genera and subgenera of the Phytoseiidae of the world (Acari: Mesostigmata), Indira Publishing House, West Bloomfied, Mich., USA. The names of the Ascidae, the Laelapidae, the Macrochelidae, the Parasitidae, the Tydeidae, the Cheyletidae, the Cunaxidae, the Erythraeidae and the Stigmaeidae are as referred to in Carrillo, D., de Moraes, G. J., Pena, J. E. (ed.) (2015) Prospects for Biological Control of Plant Feeding Mites and Other Harmful Organisms. Springer, Cham, Heidelberg, N.Y., Dordrecht, London. For *Parasitus mycophilus* reference may be made to Baker A. S., Ostoja-Starzewski J. C (2002) New distributional records of the mite *Parasitus mycophilus* (Acari: Mesostigmata), with a redescription of the male and first description of the deutonymph. Systematic & Applied Acarology 7, 113-122. For *Parasitus mammilatus* refrence may be made to Karg, W. (1993) Die Tierwelt Deutschlands, 59. Teil. Acari (Acarina), Milben Parasitiformes (Anactinochaeta) Cohors Gamasina Leach. Gustav Fischer, Jena. For the Anystidae reference may be made to Cuthbertson A. G. S., Qiu B.-L., Murchie A. K. (2014) *Anystis baccarum*: An Important Generalist Predatory Mite to be Considered in Apple Orchard Pest Management Strategies. Insects 5, 615-628; doi: 10.3390/insects5030615.

The skilled person will know the potential host range of the selected predatory mite species. Pests that may be effectively controlled with predatory mites are for example white flies, such as *Trialeurodes vaporariorum* and *Bemisia tabaci;* thrips, such as *Thrips tabaci, Thrips palmi* and *Frankliniella* spp., such as *Frankliniella occidentalis, Frankliniella schultzei* spider mites such as *Tetranychus urticae, Panonychus ulmi*, other phytophagous mites such as *Polyphagotarsonemus latus*, or other pest such as Eriophyids, Tenuipalpids, Psyllids, leathoppers, aphids, diptera. In addition mites infesting avian species, such as the red poultry mite (*Dermanyssus gallinae*) and mites infesting reptiles, such as from the family Macronyssidae, such as from the genus *Ophionyssus*, such as *Ophionyssus natricis*, may also be preyed by predatory mites, in particular predatory mites selected from the genus *Hypoaspis*, such as *Hypoaspis angusta*, from the genus *Cheyletus*, such as *Cheyletus eruditis*, from the genus *Androaelaps*, such as *Androlaelaps casalis*, from the family Laelapidae such as from the genus *Stratiolaelaps* e.g. *Stratiolaelaps scinitus* (Womersley); *Gaeolaelaps* e.g. *Gaeolaelaps aculeifer* (Canestrini); *Androlaelaps* e.g. *Androlaelaps casalis* (Berlese), or from the genus *Macrocheles*, such as *Macrocheles robustulus*.

Beneficial mites that may serve as a food source for predatory mites or other predatory arthropods according to certain embodiments of the invention may be selected from Astigmatid mites species, in particular Astigmatid mite species selected from:

i) Carpoglyphidae such as from the genus *Carpoglyphus* e.g. *Carpoglyphus lactis;* ii) Pyroglyphidae such as from the genus *Dermatophagoides* e.g. *Dermatophagoides pteronysinus, Dernmatophagoides farinae*; from the genus *Euroglyphus* e.g. *Euroglyphus longior, Euroglyphus maynei*; from the genus *Pyroglyphus* e.g. *Pyroglyphus africanus;* iii) Glycyphagidae such as from the subfamily Ctenoglyphinae, such as from the genus *Diamesoglyphus* e.g.

*Diamesoglyphus intermediusor* from the genus *Ctenoglyphus*, e.g. *Ctenoglyphus plumiger, Ctenoglyphus canestrinii, Ctenoglyphus palmifer*; the subfamily Glycyphaginae, such as from the genus *Blomnia*, e.g. *Blomia freemani* or from the genus *Glycyphagus*, e.g. *Glycyphagus ornatus, Glycphagus bicaudatus, Glycyphagus privatus, Glycyphagus domesticus*, or from the genus *Lepidoglyphus* e.g. *Lepidoglyphus michaeli, Lepidoglyphus fustifer; Lepidoglyphus destructor*, or from the genus *Austroglycyphagus*, e.g. *Austroglycyphagus geniculatus*; from the subfamily Aeroglyphinae, such as from the genus *Aeroglyphus*, e.g. *Aeroglyphus robustus*; from the subfamily Labidophorinae, such as from the genus *Gohieria*, e.g. *Gohieria fusca*; or from the subfamily Nycteriglyphinae such as from the genus *Coproglyphus*, e.g. *Coproglyphus stammeri* or from the subfamily Chortoglyphidae, such as the genus *Chortoglyphus* e.g. *Chortoglyphus arcuatus* and more preferably is selected from the subfamily Glycyphaginae, more preferably is selected from the genus *Glycyphagus* or the genus *Lepidoglyphus* most preferably selected from *Glycyphagus domesticus* or *Lepidoglyphus destructor;* iv) Acaridae such as from the genus *Tyrophagus* e.g. *Tyrophagus putrescentiae, Tyrophagus tropicus*, from the genus *Acarus* e.g. *Acarus siro, Acarus farris, Acarus gracilis*; from the genus *Lardoglyphus* e.g. *Lardoglyphus konoi*, from the genus *Thyreophagus*, such as *Thyreophagus entomophagus*; from the genus *Aleuroglyphus*, e.g. *Aleuroglyphus ovatus;* v) Suidasiidae such as from the genus *Suidasia*, such as *Suidasia nesbiti, Suidasia pontifica* or *Suidasia medanensis*.

Preferred Astigmatid mites may be selected from *Lepidoglyphus destructor*, Carpoglyphidae such as from the genus *Catpoglyphus* e.g. *Carpoglyphus lactis*, the genus *Thyreophagus*, such as *Thyreophagus entomophagus*, Acaridae, such as *Suidasia pontifica* or *Suidasia medanensis*.

Astigmatid mites can be isolated from their natural habitats as described by Hughes (Hughes, A. M., 1977, The mites of stored food and houses. Ministry of Agriculture, Fisheries and Food, Technical Bulletin No. 9: 400 pp), and can be maintained and cultured as described by Parkinson (Parkinson, C. L., 1992, "Culturing free living astigmatid mites." Arachnida: Proceedings of a one day symposium on spiders and their allies held on Saturday 21 Nov. 1987 at the Zoological Society of London) and by Solomon & Cunnington (Solomon, M. E. and Cunnington, A. M., 1963, Rearing acaroidmites, Agricultural Research Council, Pest Infestation Laboratory, Slough, England, pp 399 403).

The term "releasing" should be understood as meaning that beneficial mites may emerge from the system. Thus the mite releasing system of the invention is suitable for releasing, dispersal or providing beneficial mites. As the skilled person will understand, releasing of the beneficial mites is for introducing them in a target area where they may employ their useful function.

The system of the invention comprises a compartment, the mite compartment, holding a population of beneficial mites. A function of the compartment is to hold the individuals of the population of the beneficial mites and any additional materials associated with the beneficial mite individuals. Such additional materials may be selected from carrier materials and/or food sources known to the skilled person.

The size and shape (or form) of the compartment may vary depending on the selected beneficial mite. Selection of suitable size ranges and shapes (or forms) is within the common knowledge of the skilled person. For example reference may be made to GB2393890 and GB2509224 disclosing systems for mites or insects having suitable shapes and sizes. The skilled person will understand that the systems according to the present invention may also be designed in correspondence with the mite releasing systems as disclosed in GB2393890 and GB2509224. The mite releasing system of the invention may therefore be in association with at least one other system of the invention by being connected to the at least one other system, thus forming an association of a plurality of systems of the invention. The association of the plurality of systems of the invention preferably is such that an elongated body is formed. The elongated body preferably has a length longer than an individual system and a breadth essentially as broad as a single system. According to certain preferred embodiments the association of systems comprises 2 systems of the invention foldable to an inverted V or U, wherein the connections (the openings connecting the interior of the mite compartment with the outside space) are located inside the folded conformation. According to other preferred embodiments the association of systems has an elongated body at least 10-180 metres in length, such as 80-160 metres.

The population of beneficial mites contained in the compartment preferably is a breeding population. In this specification the term "breeding" must be understood to include the propagation and increase of a population by means of reproduction. The skilled person will know and understand that although many mite species reproduce via sexual reproduction, some species reproduce via asexual reproduction. The skilled person will be able to identify which mite species reproduce sexually and which mite species reproduce asexually. In essence a breeding population is capable of increasing the number of its individuals by means of reproduction. The skilled person will thus understand that a breeding population will comprise female mite individuals that are capable to reproduce, i.e. that can produce offspring, or female mite individuals that can mature to a life stage wherein they can produce offspring. The skilled person will further understand that for a mite species that reproduces sexually a breeding population comprises sexually mature male individuals or male individuals that may mature to sexually mature male individuals. Alternatively for a mite species reproducing sexually a breeding population may comprise one or more fertilized females.

The population of the mites preferably is in association with a carrier. The use of carriers in products comprising beneficial mites is common practice within the art and it is known that in principle any solid material which is suitable to provide a carrier surface to the individuals may be used. Therefore, in general the carrier particles will have a size larger than the size of the individuals of the beneficial mites. Preferably the carrier provides a porous medium, which allows exchange of metabolic gases and heat produced by the mite populations. The skilled person will know that the suitability of a particular carrier will depend on the species of the beneficial mite selected and will be able to select suitable carriers. For example suitable carriers may be selected from plant materials such as (wheat) bran, saw dust, corn cob grits etcetera. WO2013/103295 further discloses the suitability of chaff as a carrier material for mite populations. When a carrier is present in the mite compartment, the carrier material preferably does not fill the mite compartment completely, but there is some head space left in the mite compartment. Head space may be created by using a carrier volume of 60-95%, preferably 70-90%, more preferably 75-85% of the volume x of the mite compartment. Head space may contribute to gas exchange via the number of connections. In view of this, in case a carrier is used and there is head space in the mite compartment, the number of connections preferably are provided in the upper part of the mite compartment (where the head space will be located).

The compartment further comprises a food source for the beneficial mites. The skilled person will know that the suitability of a food source may depend on the selected species of the beneficial mite. For predatory species a living prey may be preferred. For example Astigmatid mites may be suitable prey for predatory mites. Astigmatid mite species that may be selected as food source for predatory mite species are already indicated above. Thus according to certain preferred embodiments of the invention, the mite compartment comprises a predatory mite species as the beneficial mite and an Astigmatid mite species as a food source for the predatory mite. According to further embodiments of the invention the population of Astigmatid mite species presented as a food source for the predatory mite may at least partially be immobilized as disclosed in WO2013/103294. In addition eggs from the lepidopterans *Corcyra cephalonica* or *Ephestia kuehniella* may be suitable as a food source for many mesostigmatid or prostigmatid predatory mites, such as phytoseiid predatory mites. As the skilled person will know, lepidopteran eggs are usually inactivated, when presented as as a food source to predatory mites. The skilled person will know that further food sources for predatory mites may be selected from Artemia or from pollen, such as pollen of *Typha* spp.

The mite compartment of the system of the invention is enclosed by an enclosing material, comprising a gas barrier material having a low gas exchange rate and in particular a water vapour transmission rate of ≤5, such as ≤4, ≤3, ≤2.5 g/m$^2$*24 hours. Materials with such low water vapour transmission rates also have low transmissions rates for metabolic gasses produced by the mites (and microorganisms also present in mite cultures) such as $O_2$ and/or $CO_2$. As is already indicated above, the inventors of the present invention have recently surprisingly found that contrary to the general conviction that gas permeable materials must be used in systems for releasing (providing) beneficial mites, it is possible to effectively maintain populations of species of beneficial mites in a compartment enclosed by a material having a low gas permeability. Any material having the indicated water vapour transmission rate may be suitably employed within the present invention. There is no particular lower limit for the water vapour transmission rate other than wat is technically feasible. The skilled person will know that water vapour barrier materials are available that have an infinitely small water vapour transmissions rate. Thus the water vapour transmission rate of a selected gas barrier material may be between 5.0 g/m$^2$*24 hours and the theoretical value of 0.00 g/m$^2$*24 hours. Thus according to preferred embodiments, suitable gas barrier materials may have a water vapour transmission rate between 5.0-0.01 g/m$^2$*24 hours, such as between 3.5-0.01 g/m$^2$*24 hours, between 3.5-0.5 g/m$^2$*24 hours, between 2.5-0.01 g/m$^2$*24 hours, between 2.5-0.5 g/m$^2$*24 hours, or between 2.0-0.5 g/m$^2$*24 hours. A value between 3.5-0.01 g/m$^2$*24 hours is most preferred.

The skilled person will understand that contacts and connections, such as seals, made between different parts of gas barrier material required to create the mite compartment must also be resistant to water vapour transmission in the same range as the gas barrier material. The skilled person will have knowledge how to make connections resistant to water vapour transmission. Suitable gas barrier materials preferably will further allow the creation of seals that are resistant to water vapour transmission.

Within the present description the term "compartment" refers to a part or space that is partitioned off. In the system of the present invention the space of the mite compartment is partitioned off by being enclosed by enclosing material. The reference to the mite compartment being "enclosed" by enclosing material thus means that the compartment space is surrounded by (or enveloped in) enclosing material. Enclosing material used, preferably is in sheet form, more preferably pliable sheet. The mite compartment is enclosed by a number of planes of enclosing material. For enclosing, surrounding, enveloping the mite compartment, a "number of" enclosing materials is used. Preferably a single type of enclosing material is used for all planes of enclosing material enclosing the mite compartment, such that the "number of" enclosing materials refers to an enclosing material, i.e. the singular. However, in certain alternative embodiments different types of enclosing materials may be used for different planes within the total of planes enclosing the mite compartment. For example in a sachet a front plane (where the connecting opening is located) may be from and first enclosing material and a back plane may be from a second type of enclosing material. In such cases the number of enclosing materials refers to a plurality of enclosing materials.

The term "plane" refers to a surface with any possible shape or configuration. Preferably the number of planes enclosing the mite compartment are at least essentially flat. Alternatively the planes may be curved. According to certain embodiments the planes may be of a mixed form including areas that are at least essentially flat and areas that are curved. At least essentially flat includes flat and perfectly flat.

"A number of" within this description of the present invention means one or more, such as 1, 2, 3, 4, 5, 6, 7, 8, 9, 10 or more. In certain embodiments a number of is a plurality such as 2, 4, 5, 6, 8 or 10. The number of planes of enclosing material enclosing the mite compartment may be a single plane. The skilled person will know and will understand that a single plane can form a 3-dimensional enclosure enclosing a compartment having a certain volume, if a plane is bend and fixed in a 3-dimensional enclosing structure. For example a closed compartment in shape similar to a sugar stick or coffee creamer stick may be formed from a rectangular pliable sheet bent in a cylindrical shape and fixing the sides meeting at the cylinder mantle to form a closed mantle and subsequently fixing the two opposing open ends (on "top" and "bottom" end) of the cylinder to close the open ends. The compartment in such an object is enclosed by a single plane of the enclosing material The skilled person will have knowledge as to what water vapour is and in particular that it is the gaseous state of water. The materials having the low gas exchange rate, the gas barrier materials, that are suitable for use within the present invention have a water vapour transmission rate of ≤5 g/m$^2$*24 hours. According to certain preferred embodiments the test conditions for the water vapour transmission rates are 38° C., 90% RH. Water vapour transmission rates may be determined in accordance with the procedures of the ASTM E96, the ASTM E398, or the ASTM F1249 standard. According to certain preferred embodiments, the procedures of ASTM E96 are used for determining the water vapour transmission rate. Materials having the low values of water vapour transmission as selected in the present invention also have low levels of transmission of metabolic gasses. For example the BUI43 foil (obtainable from Euroflex B. V., Zwolle, The Netherlands) according to the supplier has an oxygen permeability of about 5 cc/m²*24 hours (Measured according to ASTM F 1927 at 23° C., 50% RH). Similarly the Nativia™ NZSS films (Taghleef Industries) according to the manufacturer have an oxygen permeability of about 12 cc/m²*24 hours (Measured according to ASTM D 3985 at 23° C., 50% RH) and the EcoMet films (Ultimet Films) according to the manufacturer have an oxygen permeability of about 3.0 cc/m²*24 hours (Measured according to ASTM D 3985 at 23° C., 50% RH). Also SiOx coated barrier films, such as Ceramis® barrier films (obtainable from Amcor, Kreuzlingen, Swirserland) may suitably be selected.

Selection of a gas barrier material may be from any material having the indicated water vapour transfer rate and the skilled person will be able to select materials having a water vapour transfer rate within the indicated ranges. Multilayer laminates are preferred. As a laminate by definition should have at least 2 layers, a multilayer laminate should be understood as a laminate having at least 3 layers. Multilayer laminates in particular can be produced to have good gas barrier properties, while having additional functionality. According to certain preferred embodiments a selected gas barrier material may be a polymer-metal laminate, preferably a polymer-metal laminate film, such as a laminate film comprising a metalized polymer film. Polymer-metal laminates in particular have good gas barrier properties, in particular in case they are multi-layered. Pliable films have a particular preference as they may be more easily formed in desired shapes. A gas barrier material may for example be selected from the NatureFlex™ N932 (Innovia™ Films) film, according to the supplier having a water vapour transmission rate of <5 g/m²*24 hours (determined according to ASTM E96 at 38° C., 90% RH). However, observations made by the inventors indicate that this material may have a lower water vapour transmission rate than indicated by the supplier. Alternatively the BUI43 foil (obtainable from Euroflex B. V., Zwolle, The Netherlands) may be used. This BUI43 foil according to the supplier has a water vapour transmission rate of <1.5 g/m²*24 hours (determined according to ASTM E96 at 38° C., 90% RH). Other alternative gas barrier materials may be selected from the Nativia™ NZSS films (Taghleef Industries) that according to the supplier have a water vapour transmission rate of about 2.3 g/m²*24 hours (determined according to ASTM F1249 at 38° C., 90% RH) and the EcoMet films (Ultimet Films) that according to the supplier have a water vapour transmission rate of about 1.0 g/m²*24 hours (determined according to ASTM F1249 at 38° C., 90% RH). Although the use of these materials is particularly preferred, from the contents of this description of the invention it will be clear for the skilled person that a material other than a polymer-metal laminate, such as a polymer-metal laminate film, such as a laminate film comprising a metalized polymer film, may be selected as the gas barrier material. Metallized polymer films are also preferred in view of the fact that certain metal surfaces may maintaining water films and thus the metal layer may function as a water film maintaining material.

The number of planes of enclosing material enclosing the mite compartment will have a certain surface area z expressible in mm². The surface area referred to is the effective surface area of the barrier material that is the surface area defining (or forming the limits of) the mite compartment. This is the surface area of the enclosing material that is in contact with the interior space of the mite compartment. Depending on the specific use of the mite dispensing system, the value z of the surface area of the enclosing material may have a value selected from $0.5*10^3$-$30*10^3$ mm², preferably $2.5*10^3$-$15*10^3$ mm², more preferably $3.0*10^3$-$7.0*10^3$ mm².

The mite compartment will have a certain volume x expressible in mm³. The volume of the mite compartment is the volume of the space enclosed by the planes of enclosing material. The value x of the volume may be selected within the range of $3*10^3$ to $600*10^3$ mm³, preferably $6*10^3$ to $300*10^3$ mm³, more preferably $8*10^3$ to $100*10^3$ mm³, most preferably $9*10^3$ to $35*10$ mm³.

The system further comprises a number of connections that connect the interior space of the mite compartment with the space outside the mite compartment. The connections primarily have the functions of allowing gas exchange and to allow (mobile) individuals of the beneficial mite population to exit from the mite compartment. A number of should be construed as one or more as defined above. Openings in the enclosing material are suitable to serve as connections. Openings may be provided by any suitable means known to the skilled person, such as mechanical puncturing, such as punching or needle puncturing or, when the enclosing material has a relatively low melting temperature (below 150° C.), such as is the case for many metallised polymer films, by heat puncturing or burning. Other alternative means for creating the openings may comprise laser puncturing. Preferably a method is selected that creates openings by removal of the enclosing material.

The number of connections each will have a certain surface area y expressible in mm². The area y of a connection is the area available for gas exchange via that connection. $\Sigma y$ is the summation of the area of the individual connections in the system. For example in case a system of the invention comprises 2 connections, a first having an area y1 of 1.0 mm² and a second having an area y2 of 2.0 then $\Sigma y = y1 + y2 = 1.0 + 2.0 = 3.0$ mm². The surface area y of individual connections may have a value selected from 0.10-4.0 mm², preferably 0.15-2.0 mm², more preferably 0.20-1.5 mm², most preferably 0.20-0.50 mm². Within the indicated size ranges the shape of the connections used is such that passage of mobile mite individuals present in the mite compartment is possible through at least one of the number of connections provided. Within the broader ranges provided the skilled person will be able to select the narrower range suitable for a selected beneficial mite. Circular connections of the indicated sizes in general will be suitable for most beneficial mites. Connections of different non-circular shapes may also be suitable. Preferably non-circular connections have a shape and size that can enclose a circle having a surface area within the range mentioned for the value of y.

According to certain embodiments of the invention, the use of a plurality of connections is preferred. In case a plurality of connections is used, the number of connections may be 1 per volume fraction of the mite compartment. For example 1 per $3*10^3$ mm³ or alternatively 1 per $5*10^3$, $10*10^3$, $15*10^3$, $20*10^3$, $25*10^3$, $30*10^3$, $35*10^3$, $40*10^3$ or $50*10^3$ mm³ of volume of the mite compartment. For example for a mite compartment having a volume x of $200*10^3$ mm³, a plurality of connections may be provided such that 1 connection is provided per $20*10^3$ mm³. In this case 200/20=10 connections will be provided. Alternatively for a mite compartment having a volume x of $70*10$ mm³, a plurality of connections may be provided such that 1 connection is provided per $25*10^3$ mm³. In this case 2 connections are provided in view of the fact that 70/25=2.8 and the total number of connections that may be provided is 2. In general when using mite compartments having a volume x greater that $20*10^3$ mm$^3$, the use of a plurality of connections is preferred.

According to certain embodiments, the connections preferably are provided at an end of the system that is an upper part. Reference to an upper part refers to the situation of use of the system of the invention. In case the system of the invention is provided with means for hanging it, the upper part will be at the end of the hanging means.

In the system of the invention, the value x of the volume of the mite compartment and the value y of the area of the connections is selected such that $5*10^3$ mm$\leq$x/$\Sigma$y$\leq$70*10$^3$ mm, preferably $6*10^3$ mm$\leq$x/$\Sigma$y$\leq$60*10$^3$ mm, more preferably $7*10^3$ mm$\leq$x/$\Sigma$y$\leq$50*10$^3$ mm, wherein $\Sigma$y is the summation of the areas y of the connections. This assures that the openings are relatively small in comparison to the size of the compartment, thus limiting the escape of water vapour from the mite compartment. It is surprising that populations of mites can be effectively maintained in a closed compartment enclosed by a material having a low oxygen transmission and connected only with the exterior with connections of such a relatively small size.

In the system according to the invention (i) the water vapour transmission rate of the material enclosing the mite compartment (WVTR), the volume x of the mite compartment, the area y of the connections, and the fraction x/$\Sigma$y (wherein $\Sigma$y is the total area of the connections (the summation of the area y of the individual connections)) must be within certain predefined ranges. Selections within the ranges presented must be made such that the criteria for WVTR, x, y and x/$\Sigma$y are all within the specified ranges. In Table I below combinations of WVTR, x, y and x/$\Sigma$y envisaged within the present invention are presented. In the various columns relating to different values for the WVTR, different combinations of x, y and x/$\Sigma$y are presented. Each combination of WVTR, x, y and x/$\Sigma$y has a specific reference number I1-I338 relating to that combination. An embodiment with particular preference has the following combinations: WVTR=2.0-1.0 g/m$^2$*24 hours, x=$9*10^3$-$35*10^3$ mm$^3$, y=0.20-0.50 mm$^2$, x/$\Sigma$y=7*10-50*10$^3$ mm. A further embodiment with particular preference has the following combinations: WVTR=3.5-0.5 g/m$^2$*24 hours, x=$9*10^3$-$35*10^3$ mm$^3$, y=0.20-0.50 mm$^2$, x/$\Sigma$y=7*10-50*10$^3$ mm.

TABLE I

| WVTR (g/m$^2$*24 h) 5.0-0.00 | WVTR (g/m$^2$*24 h) 5.0-0.01 | WVTR (g/m$^2$*24 h) 3.5-0.01 | WVTR (g/m$^2$*24 h) 3.5-0.5 | WVTR (g/m$^2$*24 h) 2.5-0.01 | WVTR (g/m$^2$*24 h) 2.5-0.5 | WVTR (g/m$^2$*24 h) 2.0-0.5 |
|---|---|---|---|---|---|---|
| (I1) | (I2) | (I3) | (I4) | (I5) | (I6) | (I7) |
| x: 3k-600k y: 0.10-4.0 x/$\Sigma$y: 5k-70k | x: 3k-600k y: 0.10-4.0 x/$\Sigma$y: 5k-70k | x: 3k-600k y: 0.10-4.0 x/$\Sigma$y: 5k-70k | x: 3k-600k y: 0.10-4.0 x/$\Sigma$y: 5k-70k | x: 3k-600k y: 0.10-4.0 x/$\Sigma$y: 5k-70k | x: 3k-600k y: 0.10-4.0 x/$\Sigma$y: 5k-70k | x: 3k-600k y: 0.10-4.0 x/$\Sigma$y: 5k-70k |
| (I8) | (I9) | (I10) | (I11) | (I12) | (I13) | (I14) |
| x: 6k-300k y: 0.10-4.0 x/$\Sigma$y: 5k-70k | x: 6k-300k y: 0.10-4.0 x/$\Sigma$y: 5k-70k | x: 6k-300k y: 0.10-4.0 x/$\Sigma$y: 5k-70k | x: 6k-300k y: 0.10-4.0 x/$\Sigma$y: 5k-70k | x: 6k-300k y: 0.10-4.0 x/$\Sigma$y: 5k-70k | x: 6k-300k y: 0.10-4.0 x/$\Sigma$y: 5k-70k | x: 6k-300k y: 0.10-4.0 x/$\Sigma$y: 5k-70k |
| (I15) | (I16) | (I17) | (I18) | (I19) | (I20) | (I21) |
| x: 8k-100k y: 0.10-4.0 x/$\Sigma$y: 5k-70k | x: 8k-100k y: 0.10-4.0 x/$\Sigma$y: 5k-70k | x: 8k-100k y: 0.10-4.0 x/$\Sigma$y: 5k-70k | x: 8k-100k y: 0.10-4.0 x/$\Sigma$y: 5k-70k | x: 8k-100k y: 0.10-4.0 x/$\Sigma$y: 5k-70k | x: 8k-100k y: 0.10-4.0 x/$\Sigma$y: 5k-70k | x: 8k-100k y: 0.10-4.0 x/$\Sigma$y: 5k-70k |
| (I22) | (I23) | (I24) | (I25) | (I26) | (I27) | (I28) |
| x: 9k-35k y: 0.10-4.0 x/$\Sigma$y: 5k-70k | x: 9k-35k y: 0.10-4.0 x/$\Sigma$y: 5k-70k | x: 9k-35k y: 0.10-4.0 x/$\Sigma$y: 5k-70k | x: 9k-35k y: 0.10-4.0 x/$\Sigma$y: 5k-70k | x: 9k-35k y: 0.10-4.0 x/$\Sigma$y: 5k-70k | x: 9k-35k y: 0.10-4.0 x/$\Sigma$y: 5k-70k | x: 9k-35k y: 0.10-4.0 x/$\Sigma$y: 5k-70k |
| (I29) | (I30) | (I31) | (I32) | (I33) | (I34) | (I35) |
| x: 3k-600k y: 0.15-2.0 x/$\Sigma$y: 5k-70k | x: 3k-600k y: 0.15-2.0 x/$\Sigma$y: 5k-70k | x: 3k-600k y: 0.15-2.0 x/$\Sigma$y: 5k-70k | x: 3k-600k y: 0.15-2.0 x/$\Sigma$y: 5k-70k | x: 3k-600k y: 0.15-2.0 x/$\Sigma$y: 5k-70k | x: 3k-600k y: 0.15-2.0 x/$\Sigma$y: 5k-70k | x: 3k-600k y: 0.15-2.0 x/$\Sigma$y: 5k-70k |
| (I36) | (I37) | (I38) | (I39) | (I40) | (I41) | (I42) |
| x: 3k-600k y: 0.20-1.5 x/$\Sigma$y: 5k-70k | x: 3k-600k y: 0.20-1.5 x/$\Sigma$y: 5k-70k | x: 3k-600k y: 0.20-1.5 x/$\Sigma$y: 5k-70k | x: 3k-600k y: 0.20-1.5 x/$\Sigma$y: 5k-70k | x: 3k-600k y: 0.20-1.5 x/$\Sigma$y: 5k-70k | x: 3k-600k y: 0.20-1.5 x/$\Sigma$y: 5k-70k | x: 3k-600k y: 0.20-1.5 x/$\Sigma$y: 5k-70k |
| (I43) | (I44) | (I45) | (I46) | (I47) | (I48) | (I49) |
| x: 3k-600k y: 0.20-0.50 x/$\Sigma$y: 5k-70k | x: 3k-600k y: 0.20-0.50 x/$\Sigma$y: 5k-70k | x: 3k-600k y: 0.20-0.50 x/$\Sigma$y: 5k-70k | x: 3k-600k y: 0.20-0.50 x/$\Sigma$y: 5k-70k | x: 3k-600k y: 0.20-0.50 x/$\Sigma$y: 5k-70k | x: 3k-600k y: 0.20-0.50 x/$\Sigma$y: 5k-70k | x: 3k-600k y: 0.20-0.50 x/$\Sigma$y: 5k-70k |
| (I50) | (I51) | (I52) | (I53) | (I54) | (I55) | (I56) |
| x: 6k-300k y: 0.15-2.0 x/$\Sigma$y: 5k-70k | x: 6k-300k y: 0.15-2.0 x/$\Sigma$y: 5k-70k | x: 6k-300k y: 0.15-2.0 x/$\Sigma$y: 5k-70k | x: 6k-300k y: 0.15-2.0 x/$\Sigma$y: 5k-70k | x: 6k-300k y: 0.15-2.0 x/$\Sigma$y: 5k-70k | x: 6k-300k y: 0.15-2.0 x/$\Sigma$y: 5k-70k | x: 6k-300k y: 0.15-2.0 x/$\Sigma$y: 5k-70k |

TABLE I-continued

| WVTR (g/m²*24 h) 5.0-0.00 | WVTR (g/m²*24 h) 5.0-0.01 | WVTR (g/m²*24 h) 3.5-0.01 | WVTR (g/m²*24 h) 3.5-0.5 | WVTR (g/m²*24 h) 2.5-0.01 | WVTR (g/m²*2411) 2.5-0.5 | WVTR (g/m²*24 h) 2.0-0.5 |
|---|---|---|---|---|---|---|
| (I57) | (I58) | (I59) | (I60) | (I61) | (I62) | (I63) |
| x: 6k-300k y: 0.20-1.5 x/Σy: 5k-70k | x: 6k-300k y: 0.20-1.5 x/Σy: 5k-70k | x: 6k-300k y: 0.20-1.5 x/Σy: 5k-70k | x: 6k-300k y: 0.20-1.5 x/Σy: 5k-70k | x: 6k-300k y: 0.20-1.5 x/Σy: 5k-70k | x: 6k-300k y: 0.20-1.5 x/Σy: 5k-70k | x: 6k-300k y: 0.20-1.5 x/Σy: 5k-70k |
| (I64) | (I65) | (I66) | (I67) | (I68) | (I69) | (I70) |
| x: 6k-300k y: 0.20-0.50 x/Σy: 5k-70k | x: 6k-300k y: 0.20-0.50 x/Σy: 5k-70k | x: 6k-300k y: 0.20-0.50 x/Σy: 5k-70k | x: 6k-300k y: 0.20-0.50 x/Σy: 5k-70k | x: 6k-300k y: 0.20-0.50 x/Σy: 5k-70k | x: 6k-300k y: 0.20-0.50 x/Σy: 5k-70k | x: 6k-300k y: 0.20-0.50 x/Σy: 5k-70k |
| (I71) | (I72) | (I73) | (I74) | (I75) | (I76) | (I77) |
| x: 9k-35k y: 0.15-2.0 x/Σy: 5k-70k | x: 9k-35k y: 0.15-2.0 x/Σy: 5k-70k | x: 9k-35k y: 0.15-2.0 x/Σy: 5k-70k | x: 9k-35k y: 0.15-2.0 x/Σy: 5k-70k | x: 9k-35k y: 0.15-2.0 x/Σy: 5k-70k | x: 9k-35k y: 0.15-2.0 x/Σy: 5k-70k | x: 9k-35k y: 0.15-2.0 x/Σy: 5k-70k |
| (I78) | (I79) | (I80) | (I81) | (I82) | (I83) | (I84) |
| x: 9k-35k y: 0.20-1.5 x/Σy: 5k-70k | x: 9k-35k y: 0.20-1.5 x/Σy: 5k-70k | x: 9k-35k y: 0.20-1.5 x/Σy: 5k-70k | x: 9k-35k y: 0.20-1.5 x/Σy: 5k-70k | x: 9k-35k y: 0.20-1.5 x/Σy: 5k-70k | x: 9k-35k y: 0.20-1.5 x/Σy: 5k-70k | x: 9k-35k y: 0.20-1.5 x/Σy: 5k-70k |
| (I85) | (I86) | (I87) | (I88) | (I89) | (I90) | (I91) |
| x: 9k-35k y: 0.20-0.50 x/Σy: 5k-70k | x: 9k-35k y: 0.20-0.50 x/Σy: 5k-70k | x: 9k-35k y: 0.20-0.50 x/Σy: 5k-70k | x: 9k-35k y: 0.20-0.50 x/Σy: 5k-70k | x: 9k-35k y: 0.20-0.50 x/Σy: 5k-70k | x: 9k-35k y: 0.20-0.50 x/Σy: 5k-70k | x: 9k-35k y: 0.20-0.50 x/Σy: 5k-70k |
| (I92) | (I93) | (I94) | (I95) | (I96) | (I97) | (I98) |
| x: 3k-600k y: 0.10-4.0 x/Σy: 6k-60k | x: 3k-600k y: 0.10-4.0 x/Σy: 6k-60k | x: 3k-600k y: 0.10-4.0 x/Σy: 6k-60k | x: 3k-600k y: 0.10-4.0 x/Σy: 6k-60k | x: 3k-600k y: 0.10-4.0 x/Σy: 6k-60k | x: 3k-600k y: 0.10-4.0 x/Σy: 6k-60k | x: 3k-600k y: 0.10-4.0 x/Σy: 6k-60k |
| (I99) | (I100) | (I101) | (I102) | (I103) | (I104) | (I105) |
| x: 6k-300k y: 0.10-4.0 x/Σy: 6k-60k | x: 6k-300k y: 0.10-4.0 x/Σy: 6k-60k | x: 6k-300k y: 0.10-4.0 x/Σy: 6k-60k | x: 6k-300k y: 0.10-4.0 x/Σy: 6k-60k | x: 6k-300k y: 0.10-4.0 x/Σy: 6k-60k | x: 6k-300k y: 0.10-4.0 x/Σy: 6k-60k | x: 6k-300k y: 0.10-4.0 x/Σy: 6k-60k |
| (I106) | (I107) | (I108) | (I109) | (I110) | (I111) | (I112) |
| x: 8k-100k y: 0.10-4.0 x/Σy: 6k-60k | x: 8k-100k y: 0.10-4.0 x/Σy: 6k-60k | x: 8k-100k y: 0.10-4.0 x/Σy: 6k-60k | x: 8k-100k y: 0.10-4.0 x/Σy: 6k-60k | x: 8k-100k y: 0.10-4.0 x/Σy: 6k-60k | x: 8k-100k y: 0.10-4.0 x/Σy: 6k-60k | x: 8k-100k y: 0.10-4.0 x/Σy: 6k-60k |
| (I113) | (I114) | (I115) | (I116) | (I117) | (I118) | (I119) |
| x: 9k-35k y: 0.10-4.0 x/Σy: 6k-60k | x: 9k-35k y: 0.10-4.0 x/Σy: 6k-60k | x: 9k-35k y: 0.10-4.0 x/Σy: 6k-60k | x: 9k-35k y: 0.10-4.0 x/Σy: 6k-60k | x: 9k-35k y: 0.10-4.0 x/Σy: 6k-60k | x: 9k-35k y: 0.10-4.0 x/Σy: 6k-60k | x: 9k-35k y: 0.10-4.0 x/Σy: 6k-60k |
| (I120) | (I121) | (I122) | (I123) | (I124) | (I125) | (I126) |
| x: 3k-600k y: 0.15-2.0 x/Σy: 6k-60k | x: 3k-600k y: 0.15-2.0 x/Σy: 6k-60k | x: 3k-600k y: 0.15-2.0 x/Σy: 6k-60k | x: 3k-600k y: 0.15-2.0 x/Σy: 6k-60k | x: 3k-600k y: 0.15-2.0 x/Σy: 6k-60k | x: 3k-600k y: 0.15-2.0 x/Σy: 6k-60k | x: 3k-600k y: 0.15-2.0 x/Σy: 6k-60k |
| (I127) | (I128) | (I129) | (I130) | (I131) | (I132) | (I133) |
| x: 3k-600k y: 0.20-1.5 x/Σy: 6k-60k | x: 3k-600k y: 0.20-1.5 x/Σy: 6k-60k | x: 3k-600k y: 0.20-1.5 x/Σy: 6k-60k | x: 3k-600k y: 0.20-1.5 x/Σy: 6k-60k | x: 3k-600k y: 0.20-1.5 x/Σy: 6k-60k | x: 3k-600k y: 0.20-1.5 x/Σy: 6k-60k | x: 3k-600k y: 0.20-1.5 x/Σy: 6k-60k |
| (I134) | (I135) | (I136) | (I137) | (I138) | (I139) | (I140) |
| x: 3k-600k y: 0.20-0.50 x/Σy: 6k-60k | x: 3k-600k y: 0.20-0.50 x/Σy: 6k-60k | x: 3k-600k y: 0.20-0.50 x/Σy: 6k-60k | x: 3k-600k y: 0.20-0.50 x/Σy: 6k-60k | x: 3k-600k y: 0.20-0.50 x/Σy: 6k-60k | x: 3k-600k y: 0.20-0.50 x/Σy: 6k-60k | x: 3k-600k y: 0.20-0.50 x/Σy: 6k-60k |

TABLE I-continued

| WVTR (g/m²*24 h) 5.0-0.00 | WVTR (g/m²*24 h) 5.0-0.01 | WVTR (g/m²*24 h) 3.5-0.01 | WVTR (g/m²*24 h) 3.5-0.5 | WVTR (g/m²*24 h) 2.5-0.01 | WVTR (g/m²*24 h) 2.5-0.5 | WVTR (g/m²*24 h) 2.0-0.5 |
|---|---|---|---|---|---|---|
| (I141) | (I142) | (I143) | (I144) | (I145) | (I146) | (I147) |
| x: 6k-300k y: 0.15-2.0 x/Σy: 6k-60k | x: 6k-300k y: 0.15-2.0 x/Σy: 6k-60k | x: 6k-300k y: 0.15-2.0 x/Σy: 6k-60k | x: 6k-300k y: 0.15-2.0 x/Σy: 6k-60k | x: 6k-300k y: 0.15-2.0 x/Σy: 6k-60k | x: 6k-300k y: 0.15-2.0 x/Σy: 6k-60k | x: 6k-300k y: 0.15-2.0 x/Σy: 6k-60k |
| (I148) | (I149) | (I150) | (I151) | (I152) | (I153) | (I154) |
| x: 6k-300k y: 0.20-1.5 x/Σy: 6k-60k | x: 6k-300k y: 0.20-1.5 x/Σy: 6k-60k | x: 6k-300k y: 0.20-1.5 x/Σy: 6k-60k | x: 6k-300k y: 0.20-1.5 x/Σy: 6k-60k | x: 6k-300k y: 0.20-1.5 x/Σy: 6k-60k | x: 6k-300k y: 0.20-1.5 x/Σy: 6k-60k | x: 6k-300k y: 0.20-1.5 x/Σy: 6k-60k |
| (I155) | (I156) | (I157) | (I158) | (I159) | (I160) | (I161) |
| x: 6k-300k y: 0.20-0.50 x/Σy: 6k-60k | x: 6k-300k y: 0.20-0.50 x/Σy: 6k-60k | x: 6k-300k y: 0.20-0.50 x/Σy: 6k-60k | x: 6k-300k y: 0.20-0.50 x/Σy: 6k-60k | x: 6k-300k y: 0.20-0.50 x/Σy: 6k-60k | x: 6k-300k y: 0.20-0.50 x/Σy: 6k-60k | x: 6k-300k y: 0.20-0.50 x/Σy: 6k-60k |
| (I162) | (I163) | (I164) | (I165) | (I166) | (I167) | (I168) |
| x: 9k-35k y: 0.15-2.0 x/Σy: 6k-60k | x: 9k-35k y: 0.15-2.0 x/Σy: 6k-60k | x: 9k-35k y: 0.15-2.0 x/Σy: 6k-60k | x: 9k-35k y: 0.15-2.0 x/Σy: 6k-60k | x: 9k-35k y: 0.15-2.0 x/Σy: 6k-60k | x: 9k-35k y: 0.15-2.0 x/Σy: 6k-60k | x: 9k-35k y: 0.15-2.0 x/Σy: 6k-60k |
| (I169) | (I170) | (I171) | (I172) | (I173) | (I174) | (I175) |
| x: 9k-35k y: 0.20-1.5 x/Σy: 6k-60k | x: 9k-35k y: 0.20-1.5 x/Σy: 6k-60k | x: 9k-35k y: 0.20-1.5 x/Σy: 6k-60k | x: 9k-35k y: 0.20-1.5 x/Σy: 6k-60k | x: 9k-35k y: 0.20-1.5 x/Σy: 6k-60k | x: 9k-35k y: 0.20-1.5 x/Σy: 6k-60k | x: 9k-35k y: 0.20-1.5 x/Σy: 6k-60k |
| (I176) | (I177) | (I178) | (I179) | (I180) | (I181) | (I182) |
| x: 9k-35k y: 0.20-0.50 x/Σy: 6k-60k | x: 9k-35k y: 0.20-0.50 x/Σy: 6k-60k | x: 9k-35k y: 0.20-0.50 x/Σy: 6k-60k | x: 9k-35k y: 0.20-0.50 x/Σy: 6k-60k | x: 9k-35k y: 0.20-0.50 x/Σy: 6k-60k | x: 9k-35k y: 0.20-0.50 x/Σy: 6k-60k | x: 9k-35k y: 0.20-0.50 x/Σy: 6k-60k |
| (I183) | (I184) | (I184) | (I185) | (I186) | (I187) | (I188) |
| x: 3k-600k y: 0.10-4.0 x/Σy: 6k-60k | x: 3k-600k y: 0.10-4.0 x/Σy: 6k-60k | x: 3k-600k y: 0.10-4.0 x/Σy: 6k-60k | x: 3k-600k y: 0.10-4.0 x/Σy: 6k-60k | x: 3k-600k y: 0.10-4.0 x/Σy: 6k-60k | x: 3k-600k y: 0.10-4.0 x/Σy: 6k-60k | x: 3k-600k y: 0.10-4.0 x/Σy: 6k-60k |
| (I189) | (I190) | (I191) | (I192) | (I193) | (I194) | (I195) |
| x: 6k-300k y: 0.10-4.0 x/Σy: 6k-60k | x: 6k-300k y: 0.10-4.0 x/Σy: 6k-60k | x: 6k-300k y: 0.10-4.0 x/Σy: 6k-60k | x: 6k-300k y: 0.10-4.0 x/Σy: 6k-60k | x: 6k-300k y: 0.10-4.0 x/Σy: 6k-60k | x: 6k-300k y: 0.10-4.0 x/Σy: 6k-60k | x: 6k-300k y: 0.10-4.0 x/Σy: 6k-60k |
| (I196) | (I197) | (I198) | (I199) | (I200) | (I201) | (I202) |
| x: 8k-100k y: 0.10-4.0 x/Σy: 6k-60k | x: 8k-100k y: 0.10-4.0 x/Σy: 6k-60k | x: 8k-100k y: 0.10-4.0 x/Σy: 6k-60k | x: 8k-100k y: 0.10-4.0 x/Σy: 6k-60k | x: 8k-100k y: 0.10-4.0 x/Σy: 6k-60k | x: 8k-100k y: 0.10-4.0 x/Σy: 6k-60k | x: 8k-100k y: 0.10-4.0 x/Σy: 6k-60k |
| (I203) | (I204) | (I205) | (I206) | (I207) | (I208) | (I209) |
| x: 9k-35k y: 0.10-4.0 x/Σy: 6k-60k | x: 9k-35k y: 0.1.0-4.0 x/Σy: 6k-60k | x: 9k-35k y: 0.10-4.0 x/Σy: 6k-60k | x: 9k-35k y: 0.10-4.0 x/Σy: 6k-60k | x: 9k-35k y: 0.10-4.0 x/Σy: 6k-60k | x: 9k-35k y: 0.10-4.0 x/Σy: 6k-60k | x: 9k-35k y: 0.10-4.0 x/Σy: 6k-60k |
| (I210) | (I211) | (I212) | (I213) | (I214) | (I215) | (I216) |
| x: 3k-600k y: 0.10-4.0 x/Σy: 7k-50k | x: 3k-600k y: 0.10-4.0 x/Σy: 7k-50k | x: 3k-600k y: 0.10-4.0 x/Σy: 7k-50k | x: 3k-600k y: 0.10-4.0 x/Σy: 7k-50k | x: 3k-600k y: 0.10-4.0 x/Σy: 7k-50k | x: 3k-600k y: 0.10-4.0 x/Σy: 7k-50k | x: 3k-600k y: 0.10-4.0 x/Σy: 7k-50k |
| (I217) | (I218) | (I219) | (I220) | (I221) | (I222) | (I223) |
| x: 6k-300k y: 0.10-4.0 x/Σy: 7k-50k | x: 6k-300k y: 0.10-4.0 x/Σy: 7k-50k | x: 6k-300k y: 0.10-4.0 x/Σy: 7k-50k | x: 6k-300k y: 0.10-4.0 x/Σy: 7k-50k | x: 6k-300k y: 0.10-4.0 x/Σy: 7k-50k | x: 6k-300k y: 0.10-4.0 x/Σy: 7k-50k | x: 6k-300k y: 0.10-4.0 x/Σy: 7k-50k |

TABLE I-continued

| WVTR (g/m²*24 h) 5.0-0.00 | WVTR (g/m²*24 h) 5.0-0.01 | WVTR (g/m²*24 h) 3.5-0.01 | WVTR (g/m²*24 h) 3.5-0.5 | WVTR (g/m²*24 h) 2.5-0.01 | WVTR (g/m²*24 h) 2.5-0.5 | WVTR (g/m²*24 h) 2.0-0.5 |
|---|---|---|---|---|---|---|
| (I224) | (I225) | (I226) | (I227) | (I228) | (I229) | (I230) |
| x: 8k-100k y: 0.10-4.0 x/Σy: 7k-50k | x: 8k-100k y: 0.10-4.0 x/Σy: 7k-50k | x: 8k-100k y: 0.10-4.0 x/Σy: 7k-50k | x: 8k-100k y: 0.10-4.0 x/Σy: 7k-50k | x: 8k-100k y: 0.10-4.0 x/Σy: 7k-50k | x: 8k-100k y: 0.10-4.0 x/Σy: 7k-50k | x: 8k-100k y: 0.10-4.0 x/Σy: 7k-50k |
| (I231) | (I232) | (I233) | (I234) | (I235) | (I236) | (I237) |
| x: 9k-35k y: 0.10-4.0 x/Σy: 7k-50k | x: 9k-35k y: 0.10-4.0 x/Σy: 7k-50k | x: 9k-35k y: 0.10-4.0 x/Σy: 7k-50k | x: 9k-35k y: 0.10-4.0 x/Σy: 7k-50k | x: 9k-35k y: 0.10-4.0 x/Σy: 7k-50k | x: 9k-35k y: 0.10-4.0 x/Σy: 7k-50k | x: 9k-35k y: 0.10-4.0 x/Σy: 7k-50k |
| (I238) | (I239) | (I240) | (I241) | (I242) | (I243) | (I244) |
| x: 3k-600k y: 0.15-2.0 x/Σy: 7k-50k | x: 3k-600k y: 0.15-2.0 x/Σy: 7k-50k | x: 3k-600k y: 0.15-2.0 x/Σy: 7k-50k | x: 3k-600k y: 0.15-2.0 x/Σy: 7k-50k | x: 3k-600k y: 0.15-2.0 x/Σy: 7k-50k | x: 3k-600k y: 0.15-2.0 x/Σy: 7k-50k | x: 3k-600k y: 0.15-2.0 x/Σy: 7k-50k |
| (I245) | (I246) | (I247) | (I248) | (I249) | (I250) | (I251) |
| x: 3k-600k y: 0.20-1.5 x/Σy: 7k-50k | x: 3k-600k y: 0.20-1.5 x/Σy: 7k-50k | x: 3k-600k y: 0.20-1.5 x/Σy: 7k-50k | x: 3k-600k y: 0.20-1.5 x/Σy: 7k-50k | x: 3k-600k y: 0.20-1.5 x/Σy: 7k-50k | x: 3k-600k y: 0.20-1.5 x/Σy: 7k-50k | x: 3k-600k y: 0.20-1.5 x/Σy: 7k-50k |
| (I252) | (I253) | (I254) | (I255) | (I256) | (I257) | (I258) |
| x: 3k-600k y: 0.20-0.50 x/Σy: 7k-50k | x: 3k-600k y: 0.20-0.50 x/Σy: 7k-50k | x: 3k-600k y: 0.20-0.50 x/Σy: 7k-50k | x: 3k-600k y: 0.20-0.50 x/Σy: 7k-50k | x: 3k-600k y: 0.20-0.50 x/Σy: 7k-50k | x: 3k-600k y: 0.20-0.50 x/Σy: 7k-50k | x: 3k-600k y: 0.20-0.50 x/Σy: 7k-50k |
| (I259) | (I260) | (I271) | (I272) | (I273) | (I274) | (I275) |
| x: 6k-300k y: 0.15-2.0 x/Σy: 7k-50k | x: 6k-300k y: 0.15-2.0 x/Σy: 7k-50k | x: 6k-300k y: 0.15-2.0 x/Σy: 7k-50k | x: 6k-300k y: 0.15-2.0 x/Σy: 7k-50k | x: 6k-300k y: 0.15-2.0 x/Σy: 7k-50k | x: 6k-300k y: 0.15-2.0 x/Σy: 7k-50k | x: 6k-300k y: 0.15-2.0 x/Σy: 7k-50k |
| (I276) | (I277) | (I278) | (I279) | (I280) | (I281) | (I282) |
| x: 6k-300k y: 0.20-1.5 x/Σy: 7k-50k | x: 6k-300k y: 0.20-1.5 x/Σy: 7k-50k | x: 6k-300k y: 0.20-1.5 x/Σy: 7k-50k | x: 6k-300k y: 0.20-1.5 x/Σy: 7k-50k | x: 6k-300k y: 0.20-1.5 x/Σy: 7k-50k | x: 6k-300k y: 0.20-1.5 x/Σy: 7k-50k | x: 6k-300k y: 0.20-1.5 x/Σy: 7k-50k |
| (I283) | (I284) | (I285) | (I286) | (I287) | (I288) | (I289) |
| x: 6k-300k y: 0.20-0.50 x/Σy: 7k-50k | x: 6k-300k y: 0.20-0.50 x/Σy: 7k-50k | x: 6k-300k y: 0.20-0.50 x/Σy: 7k-50k | x: 6k-300k y: 0.20-0.50 x/Σy: 7k-50k | x: 6k-300k y: 0.20-0.50 x/Σy: 7k-50k | x: 6k-300k y: 0.20-0.50 x/Σy: 7k-50k | x: 6k-300k y: 0.20-0.50 x/Σy: 7k-50k |
| (I290) | (I291) | (I292) | (I293) | (I294) | (I295) | (I296) |
| x: 9k-35k y: 0.15-2.0 x/Σy: 7k-50k | x: 9k-35k y: 0.15-2.0 x/Σy: 7k-50k | x: 9k-35k y: 0.15-2.0 x/Σy: 7k-50k | x: 9k-35k y: 0.15-2.0 x/Σy: 7k-50k | x: 9k-35k y: 0.15-2.0 x/Σy: 7k-50k | x: 9k-35k y: 0.15-2.0 x/Σy: 7k-50k | x: 9k-35k y: 0.15-2.0 x/Σy: 7k-50k |
| (I297) | (I298) | (I299) | (I300) | (I301) | (I302) | (I303) |
| x: 9k-35k y: 0.20-1.5 x/Σy: 7k-50k | x: 9k-35k y: 0.20-1.5 x/Σy: 7k-50k | x: 9k-35k y: 0.20-1.5 x/Σy: 7k-50k | x: 9k-35k y: 0.20-1.5 x/Σy: 7k-50k | x: 9k-35k y: 0.20-1.5 x/Σy: 7k-50k | x: 9k-35k y: 0.20-1.5 x/Σy: 7k-50k | x: 9k-35k y: 0.20-1.5 x/Σy: 7k-50k |
| (I304) | (I305) | (I306) | (I307) | (I308) | (I309) | (I310) |
| x: 9k-35k y: 0.20-0.50 x/Σy: 7k-50k | x: 9k-35k y: 0.20-0.50 x/Σy: 7k-50k | x: 9k-35k y: 0.20-0.50 x/Σy: 7k-50k | x: 9k-35k y: 0.20-0.50 x/Σy: 7k-50k | x: 9k-35k y: 0.20-0.50 x/Σy: 7k-50k | x: 9k-35k y: 0.20-0.50 x/Σy: 7k-50k | x: 9k-35k y: 0.20-0.50 x/Σy: 7k-50k |
| (I311) | (I312) | (I313) | (I314) | (I315) | (I316) | (I317) |
| x: 3k-600k y: 0.10-4.0 x/Σy: 7k-50k | x: 3k-600k y: 0.10-4.0 x/Σy: 7k-50k | x: 3k-600k y: 0.10-4.0 x/Σy: 7k-50k | x: 3k-600k y: 0.10-4.0 x/Σy: 7k-50k | x: 3k-600k y: 0.10-4.0 x/Σy: 7k-50k | x: 3k-600k y: 0.10-4.0 x/Σy: 7k-50k | x: 3k-600k y: 0.10-4.0 x/Σy: 7k-50k |

TABLE I-continued

| WVTR (g/m²*24 h) 5.0-0.00 | WVTR (g/m²*24 h) 5.0-0.01 | WVTR (g/m²*24 h) 3.5-0.01 | WVTR (g/m²*24 h) 3.5-0.5 | WVTR (g/m²*24 h) 2.5-0.01 | WVTR (g/m²*2411) 2.5-0.5 | WVTR (g/m²*24 h) 2.0-0.5 |
|---|---|---|---|---|---|---|
| (I318) | (I319) | (I320) | (I321) | (I322) | (I323) | (I324) |
| x: 6k-300k y: 0.10-4.0 x/Σy: 7k-50k | x: 6k-300k y: 0.10-4.0 x/Σy: 7k-50k | x: 6k-300k y: 0.10-4.0 x/Σy: 7k-50k | x: 6k-300k y: 0.10-4.0 x/Σy: 7k-50k | x: 6k-300k y: 0.10-4.0 x/Σy: 7k-50k | x: 6k-300k y: 0.10-4.0 x/Σy: 7k-50k | x: 6k-300k y: 0.10-4.0 x/Σy: 7k-50k |
| (I325) | (I326) | (I327) | (I328) | (I329) | (I330) | (I331) |
| x: 8k-100k y: 0.10-4.0 x/Σy: 7k-50k | x: 8k-100k y: 0.10-4.0 x/Σy: 7k-50k | x: 8k-100k y: 0.10-4.0 x/Σy: 7k-50k | x: 8k-100k y: 0.10-4.0 x/Σy: 7k-50k | x: 8k-100k y: 0.10-4.0 x/Σy: 7k-50k | x: 8k-100k y: 0.10-4.0 x/Σy: 7k-50k | x: 8k-100k y: 0.10-4.0 x/Σy: 7k-50k |
| (I332) | (I333) | (I334) | (I335) | (I336) | (I337) | (I338) |
| x: 9k-35k y: 0.10-4.0 x/Σy: 7k-50k | x: 9k-35k y: 0.10-4.0 x/Σy: 7k-50k | x: 9k-35k y: 0.10-4.0 x/Σy: 7k-50k | x: 9k-35k y: 0.10-4.0 x/Σy: 7k-50k | x: 9k-35k y: 0.10-4.0 x/Σy: 7k-50k | x: 9k-35k y: 0.10-4.0 x/Σy: 7k-50k | x: 9k-35k y: 0.10-4.0 x/Σy: 7k-50k | k = *10³

The skilled person will understand that under force the volume of a body can change. This is in particular the case for bodies made of pliable material, such as pliable film. In case of the use of pliable materials the volume of the mite compartment may vary between the volume of the material present in the mite compartment (e.g. the mite composition comprising the individuals of the mite population and often a carrier) and the maximal volume that the material enclosing the mite compartment, the gas barrier material, may provide on the basis of its dimensions and/or geometrical restrictions. Thus for mite releasing systems using pliable gas barrier material, the value x, may not be fixed but may vary. For such systems the relevant volume of the mite compartment to take into consideration for determining the x/Σy ratio is the volume the mite compartment has during a substantial amount of time, such as during at least 12 hours, such as at least 18 hours.

The enclosing material used preferably is opaque, thus preventing light to enter the mite compartment. This is beneficial to prevent heat absorption from visible light in the mite compartment. The NatureFlex™ N932 (Innovia™ Films) film and the BUI43 foil (obtainable from Euroflex B. V., Zwolle, The Netherlands) are examples of materials having opaque properties.

In view of sustainable use of the system of the invention, it is further preferred that the system is made from compostable materials. The use of compostable enclosing materials in this respect is preferred. The NatureFlex™ N932 (Innovia™ Films) film and the BUI43 foil (obtainable from Euroflex B. V., Zwolle, The Netherlands) are examples of compostable materials having suitable properties.

The system for releasing beneficial mites according to the present invention is characterized in that the outer surface of the enclosing material comprises a water film maintaining material. As is already discussed above, careful analysis of the problem, of water entry into the mite compartment of mite releasing systems comprising gas barrier materials, and the solution, provided by a paper layer on the outer surface of the mite releasing system, has brought the inventors of the present invention to the conclusion that the risk of water inflow into the mite compartment is reduced by using on the outer surface of the mite releasing system a water film maintaining material. Without wishing to be bound by any theory, it is believed that water on contacting the paper surface is absorbed into the (micro)pores of the paper. It is believed that not all water molecules will be absorbed into the interior of the paper layer and a certain amount of water molecules will remain at the surface of the paper layer (in particular upon saturation of the porous structure of the paper layer) where they present hydrophilic contact points available for contact with materials presented to the surface of the paper, such as further water molecules. It may be theorized that this surface water may be somewhat restricted in its movement by being connected to water in the interior of the (micro)pores of the paper. Thus when further amounts of water are presented to the surface, this incoming water will experience a hydrophilic surface (having a relatively high surface energy) formed by the surface water on the paper surface. Water drops introduced to this surface (having a relatively high surface energy due to the presence of surface water), will have a small (or even zero) Young contact angle and thus will spread and form a water film. This results in a different way wherein water on the outer surface of the mite releasing system behaves in comparison to the recently developed mite releasing system constructed from the metallized polymer film foil BUI43 (obtainable from Euroflex B. V., Zwolle, The Netherlands) which cannot maintain a water film. As is shown in the experimental section, this differing way of water flow surprisingly reduces the risk of entry of water from the exterior into the mite compartment.

On the basis of the above described theoretical hypotheses it may be expected that any material capable of maintaining a water film, will have an effect in reducing the risk of water entry into the mite compartment. It may also be expected that any material comprising a porous surface capable of absorption of water may be used as a water film maintaining material. The skilled person will however also understand that non-porous surfaces having a sufficiently high surface free energy (thus having a relatively small Young contact angle for water) will also be able to maintain a water film and may be suitably employed as a water film maintaining material in the present invention.

Figures 8, 9:
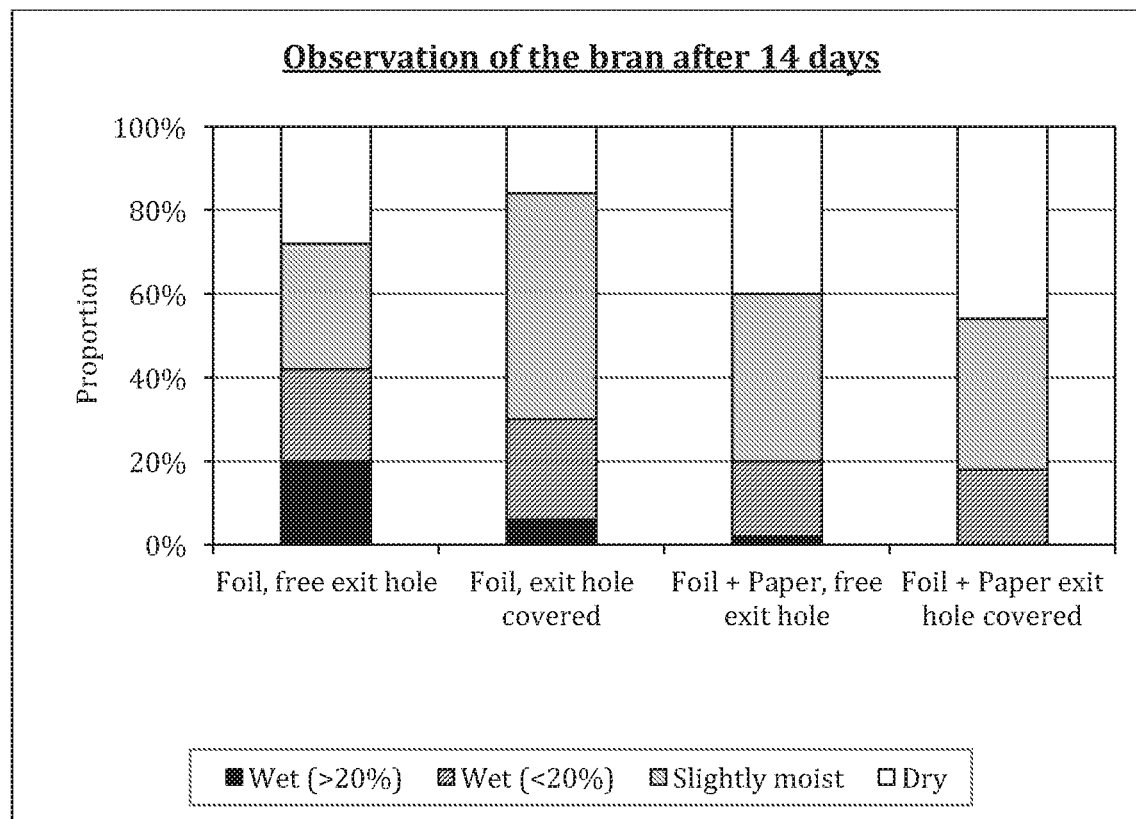
FIG. 8, shows the composition of the irrigation water used in the experiments.
FIG. 9 shows the results of the observation of bran after 14 days of experiment 2.

The meaning of the term "maintaining" as "to keep in existence" or "to keep in a specified state" will be known to the skilled person. Within the context of the present invention a water film maintaining material therefore is a material on which water, when present on said water film maintaining material, is able to maintain the form of a film. Water may not always spontaneously form a film on a given surface, therefore sometimes a certain force is required to bring water in the form of a film. It is therefore preferred according to certain embodiments that the water maintains the form of a film after mechanically being forced into the form of a film. On the basis of his common general knowledge and the description of the present invention, the skilled person will know and understand that a "water film" in the context of this invention should be considered in the context of surface wetting theory. On the basis of his knowledge of wetting theory and the description of the present invention, the skilled person will know and understand that within the present invention the term "water film" on the one hand relates to (partially) wetting films of water, meaning a water film having wetting interaction with a surface, as is known in wetting theory, and on the other hand to water films formed on a water absorbing (saturated) porous surface. The skilled person will understand from this description of the invention that wetting films of water and water films formed on a water absorbing (saturated) porous surface may have similar properties, in particular in respect of their interaction with additional water (drops) contacting the water film. On the basis of his knowledge of wetting theory and the description of the present invention, the skilled person will also be able to evaluate and determine if a water film is maintained on a certain surface for example by using the test presented in the experimental section and/or a test performed similar to a 'water break test' e.g. performed in analogy with ASTM F22. The skilled person will know and understand that water films cannot be effectively maintained on any material. For example it is known that hydrophobic surfaces are not able to support a water film. And that instead a certain degree of hydrophilicity of the surface is required for maintaining a water film or that alternatively the material must comprise a (micro) porous structure wherein water may be absorbed while water remains on the surface of the porous structure e.g. by saturation of the porous structure with water and/or by the forces of the surface tension of water in the pores. The skilled person will thus be able to select suitable water film maintaining materials from a water absorbing porous material or from a material having a sufficiently high surface free energy (thus having a relatively small Young contact angle for water). For this the skilled person may also revert to the test presented in the experimental section and/or to a test performed in analogy with a 'water break test' e.g. performed in analogy with ASTM F22. The water referred to can be any water (solution) relevant in the use of the mite releasing system, such as pure water, rain water, condensation water, tap water, fertilized rain water or fertilized tap water or other irrigation water. Fertilized water is a mineral solution of water frequently used in horticulture and comprises dissolved minerals as inorganic (micro) nutrients for plants. The skilled person will be able to prepare fertilized water. A typical composition of fertilized water is presented in the table of FIG. 8. Although on a theoretical level there may be minor differences between the contact angle of the different water solutions with a specific material, the skilled person will also understand that there is little practical relevance for those differences, in particular when the contact angle is already low, e.g. ≤45°. According to a preferred embodiment water is ultrapure distilled water. According to different preferred embodiment water is fertilized rain water, in particular fertilized rain water having the composition presented in FIG. 8. The water film maintaining material preferably is an outer surface layer in a laminate comprising the gas barrier material.

According to a preferred embodiment, the water-film maintaining material comprises a porous material capable of absorption of water. The skilled person will know and understand what a porous material is. He will thus know and understand that a porous material is a material comprising pores. A pore being a minute opening or orifice or a minute interstice. The porosity of the porous material according to certain embodiments is between 0.5 and 0.9, preferably between 0.5 and 0.85. It is further preferred that the water absorbing porous material is a microporous material. According to the present invention a microporous material is a material having an average pore diameter ranging from 5-100 µm, preferably 5-60 µm.

The porous material capable of absorption of water preferably is an outer surface layer incorporated in a laminate comprising the gas barrier material. The skilled person will be able to select suitable porous materials capable of absorption of water. According to certain preferred embodiments the porous materials capable of absorption of water may be a layer of a fibrous material. As the skilled person will understand porous fibrous materials have pores formed between the fibres. The layer of fibrous material preferably is a layer of pressed plant fibres. The plant fibres preferably are cellulose fibres. Most preferably the layer of pressed plant fibres is paper. Any type of paper suitable for absorption of water may be used. Kraft paper has been proven to have good functionality and similar types of paper may be employed. The weight of the paper used may for example be between 15 and 50 g/m$^2$.

Paper being the preferred porous water absorbing material, it is preferred that alternative water absorbing porous material have similar characteristics, in particular in respect of the layer thickness, porosity and pore size. It is thus preferred that the water absorbing porous material is a sheet material having an average layer thickness of 20-500 µm, more preferably 50-200 µm. A preferred porous material has a layer thickness of 50-200 µm, and an average pore diameter from 5-60 µm. A further preferred porous material has a layer thickness of 50-200 µm, a porosity of 0.5-0.85 and an average pore diameter from 5-60 µm. Certain preferred embodiments of the mite releasing system envisaged by the invention have a gas barrier material having a water vapour transmission rate of ≤3, such as ≤2.5 g/m$^2$*24 hours, an outer surface of the enclosing material comprising a water film maintaining material selected from a water absorbing porous material having a layer thickness of 50-200 µm, an average pore diameter from 5-60 µm, optionally a porosity of 0.5-0.85, and a combination of WVTR, x, y and x/Σy according to reference number I1-I338, that is I1 or I2 or I3 or I4 or I5 or I6 or I7 or I8 or I9 or I10 or I11 or I12 or I13 or I14 or I15 or I16 or I17 or I18 or I19 or I20 or I21 or I22 or I23 or I24 or I25 or I26 or I27 or I28 or I29 or I30 or I31 or I32 or I33 or I34 or I35 or I36 or I37 or I38 or I39 or I40 or I41 or I42 or I43 or I44 or I45 or I46 or I47 or I48 or I49 or I50 or I51 or I52 or I53 or I54 or I55 or I56 or I57 or I58 or I59 or I60 or I61 or I62 or I63 or I64 or I65 or I66 or I67 or I68 or I69 or I70 or I71 or I72 or I73 or I74 or I75 or I76 or I77 or I78 or I79 or I80 or I81 or I82 or I83 or I84 or I85 or I86 or I87 or I88 or I89 or I90 or I91 or I92 or I93 or I94 or I95 or I96 or I97 or I98 or I99 or I100 or I101 or I102 or I103 or I104 or I105 or I106 or I107 or I108 or I109 or I110 or I111 or I112 or I113 or I114 or I115 or I116 or I117 or I118 or I119 or I120 or I121 or I122 or I123 or I124 or I125 or I126 or I127 or I128 or I129 or I130 or I131 or I132 or I133 or I134 or I135 or I136 or I137 or I138 or I139 or I140 or I141 or I142 or I143 or I144 or I145 or I146 or I147 or I148 or I149 or I150 or I151 or I152 or I153 or I154 or I155 or I156 or I157 or I158 or I159 or I160 or I61 or I162 or I163 or I164 or I165 or I166 or I167 or I168 or I169 or I170 or I171 or I172 or I173 or I174 or I175 or I176 or I177 or I178 or I179 or I180 or I181 or I182 or I183 or I184 or I185 or I186 or I187 or I188 or I189 or I190 or I191 or I192 or I193 or I194 or I195 or I196 or I197 or I198 or I199 or I200 or I201 or I202 or I203 or I204 or I205 or I206 or I207 or I208 or I209 or I210 or I211 or I212 or I213 or I214 or I215 or I216 or I217 or I218 or I219 or I220 or I221 or I222 or I223 or I224 or I225 or I226 or I227 or I228 or I229 or I230 or I231 or I232 or I233 or I234 or I235 or I236 or I237 or I238 or I239 or I240 or I241 or I242 or I243 or I244 or I245 or I246 or I247 or I248 or I249 or I250 or I251 or I252 or I253 or I254 or I255 or I256 or I257 or I258 or I259 or I260 or I261 or I262 or I263 or I264 or I265 or I266 or I267 or I268 or I269 or I270 or I271 or I272 or I273 or I274 or I275 or I276 or I277 or I278 or I279 or I280 or I281 or I282 or I283 or I284 or I285 or I286 or I287 or I288 or I289 or I290 or I291 or I292 or I293 or I294 or I295 or I296 or I297 or I298 or I299 or I300 or I301 or I302 or I303 or I304 or I305 or I306 or I307 or I308 or I309 or I310 or I311 or I312 or I313 or I314 or I315 or I316 or I317 or I318 or I319 or I320 or I321 or I322 or I323 or I324 or I325 or I326 or I327 or I328 or I329 or I330 or I331 or I332 or I333 or I334 or I335 or I336 or I337 or I338, from table I. In these embodiments the water film maintaining material preferably is in a laminate comprising the gas barrier material. For the further aspects of the invention, the use of these embodiments of the mite releasing system are also preferred according to certain embodiments.

The structure of the porous material may be formed by a hydrophilic or a hydrophobic material. The use of a hydrophilic material is preferred as this further increases the interactions with water.

As the skilled person will appreciate, on the basis of the above presented theory and his common general knowledge, an alternative water film maintaining material is a material having relatively good wetting properties, such as a non-hydrophobic material. Wetting being the ability of a liquid to maintain contact with a solid surface. As the skilled person will know, wettability of a surface by a liquid is correlated to the Young contact angle $\theta$ of water on the surface. According to certain embodiments the water film maintaining material is selected such that water has a Young contact angle $\theta$ of at most 60°, such as ≤60°, ≤55°, ≤50°, ≤45°, ≤40°, ≤35°, ≤30°, ≤35°, ≤30°, ≤25°, ≤20°, ≤15°, ≤10°, ≤5°, such as 0° on the surface of the water film maintaining material. In view of the fact that complete wetting occurs when the Young contact angle $\theta$ equals zero, the lower the value of $\theta$, the higher the degree of wetting. It is preferred that the water film maintaining material is selected such that water has a Young contact angle $\theta$ of ≤50°, more preferably ≤45°, even more preferably ≤40°, still more preferably ≤35°, most preferably ≤20°, such as ≤15°, ≤10°, or ≤5°. The skilled person will know the procedures for determine the Young contact angle of water on a surface of a certain material, such as a treated or non-treated polymeric material or a non-polymeric material. For example the methodology of ASTM-5946 or an analogous method can be used. As the skilled person will understand, although the methodology of this standard is aimed at measuring contact angles for corona treated polymers, the general methodology is equally suitable for measuring contact angles with water for different surfaces. The Young contact angle according to preferred embodiments is determined under standard test conditions of ASTM 5946, viz. at atmospheric pressure, 23° C. and 50% relative humidity. In accordance with other preferred embodiments the Young contact angle is determined according to ASTM D-5946 with the modification that the test surface may be a Corona-Treated Polymer film or a surface different from a Corona-Treated Polymer film. The material selected such that water has a Young contact angle $\theta$ of ≤50, according to preferred embodiments has a non-porous surface.

The skilled person will be able to select suitable materials having a Young contact angle with water of ≤60°. Using the standard tests available in the art the contact angle of a material with water may be determined and thus the suitability of the material may be determined. Suitable materials may for example be selected from metals, preferably metal films, (modified) polymers, such as corona or plasma treated polymers (see e.g. Jorda-Vilaplana et al., European Polymer Journal, Volume 58, September 2014, Pages 23-33), preferably polymers films or surfaces treated with a hydrophilic material such as surfaces provided with a wetting agent such as surfaces provided with a hydrophilic coating, for example a hydrophilic coating on the basis of $TiO_2$ or a different hydrophilic compound. The skilled person will know and understand that and how hydrophilic coatings may increase the wettability of a surface of a material. According to a preferred embodiment the enclosing material is a laminate wherein the gas barrier material comprises a metalized polymer film and the water film maintaining material is a polymer modified by a surface treatment increasing the surface energy, such as a treatment selected from corona treatment, plasma treatment or hydrophilic coating, such as a titanium oxide coating.

Certain embodiments of the mite releasing system envisaged by the invention have a gas barrier material having a water vapour transmission rate of ≤3, such as ≤2.5 g/m²*24 hours, a water film maintaining material selected such that water has a Young contact angle $\theta$ of ≤45°, more preferably ≤40°, still more preferably ≤35°, most preferably ≤20°, such as ≤15°, ≤10°, or ≤5° on the surface of the water film maintaining material and further have a combination of WVTR, x, y and x/Σy according to reference number I1 or I2 or I3 or I4 or I5 or I6 or I7 or I8 or I9 or I10 or I11 or I12 or I13 or I14 or I15 or I16 or I17 or I18 or I19 or I20 or 21 or I22 or I23 or I24 or I25 or I26 or I27 or I28 or I29 or I30 or I31 or I32 or I33 or I34 or I35 or I36 or I37 or I38 or I39 or I40 or I41 or I42 or I43 or I44 or I45 or I46 or I47 or I48 or I49 or I50 or I51 or I52 or I53 or I54 or I55 or I56 or I57 or I58 or I59 or I60 or I161 or I62 or I63 or I64 or I65 or I66 or I67 or I68 or I69 or I70 or I71 or I72 or I73 or I74 or I75 or I76 or I77 or I78 or I79 or I80 or 81 or I82 or I83 or I84 or I85 or I86 or I87 or I88 or I89 or I90 or I91 or I92 or I93 or I94 or I95 or I96 or I97 or I98 or I99 or I100 or I101 or I102 or I103 or I104 or I105 or I106 or I107 or I108 or I109 or I110 or I111 or I112 or I113 or I114 or I115 or I116 or I117 or I118 or I119 or I120 or I121 or I122 or I123 or I124 or I125 or I126 or I127 or I128 or I129 or I130 or I131 or I132 or I133 or I134 or I135 or I136 or I137 or I138 or I139 or I140 or I141 or I142 or I143 or I144 or I145 or I146 or I147 or I148 or I149 or I150 or I151 or I152 or I153 or I154 or I155 or I156 or I157 or I158 or I159 or I160 or I161 or I162 or I163 or I164 or I165 or I166 or I167 or I168 or I169 or I170 or I171 or I172 or I173 or I174 or I175 or I176 or I177 or I178 or I179 or I180 or I181 or I182 or I183 or I184 or I185 or I186 or I187 or I188 or I189 or I190 or I191 or I192 or I193 or I194 or I195 or I196 or I197 or I198 or I199 or I200 or I201 or I202 or I203 or I204 or I205 or I206 or I207 or I208 or I209 or I210 or I211 or I212 or I213 or I214 or I215 or I216 or I217 or I218 or I219 or I220 or I221 or I222 or I223 or I224 or I225 or I226 or I227 or I228 or I229 or I230 or I231 or I232 or I233 or I234 or I235 or I236 or I237 or I238 or I239 or I240 or I241 or I242 or I243 or I244 or I245 or I246 or I247 or I248 or I249 or I250 or I251 or I252 or I253 or I254 or I255 or I256 or I257 or I258 or I259 or I260 or I261 or I262 or I263 or I264 or I265 or I266 or I267 or I268 or I269 or I270 or I271 or I272 or I273 or I274 or I275 or I276 or I277 or I278 or I279 or I280 or I281 or I282 or I283 or I284 or I285 or I286 or I287 or I288 or I289 or I290 or I291 or I292 or I293 or I294 or I295 or I296 or I297 or I298 or I299 or I300 or I301 or I302 or I303 or I304 or I305 or I306 or I307 or I308 or I309 or I310 or I311 or I312 or I313 or I314 or I315 or I316 or I317 or I318 or I319 or I320 or I321 or I322 or I323 or I324 or I325 or I326 or I327 or I328 or I329 or I330 or I331 or I332 or I333 or I334 or I335 or I336 or I337 or I338 from table I. In these embodiments the water film maintaining material preferably is in a laminate comprising the gas barrier material. For the further aspects of the invention, the use of these embodiments of the mite releasing system are also preferred according to certain embodiments.

The skilled person will know that there is a correlation between the contact angle and the surface free energy and that the wetting energy is a derivative of the surface free energy. Therefore, according to certain embodiments the water-film maintaining material is a material having a surface free energy of at least 43 dyne/cm, such as ≥44, ≥45, ≥50, ≥55, ≥60, ≥65, ≥70, ≥75 dyne/cm. The skilled person will know and understand the term surface free energy (or alternatively surface energy or interface energy). As the skilled person will also know, the wetting by water increases when the surface free energy increases. According to theory, when the surface free energy of a surface is larger than the surface tension of the liquid, wetting of the surface by the liquid is maximal as the Young contact angle θ is zero under these circumstances. Water has a surface tension of around 72 dyne/cm under standard conditions (see e.g. Jorda-Vilaplana et al., European Polymer Journal, Volume 58, September 2014, Pages 23-33). The higher values of the surface tension are thus preferred. Thus preferably the surface tension of the water film maintaining material is ≥42 or ≥45, more preferably ≥50 or ≥55, even more preferably ≥60 or ≥65 and most preferably ≥70 or ≥75 dyne/cm. There is no upper limit for the surface energy value, other than what is possible in practice. According to certain preferred embodiments the water film maintaining material has a surface energy of at most 1000 dyne/cm, such as at most 500 dyne/cm, such as at most 200 dyne/cm, such as at most 150 dyne/cm, such as at most 100 dyne/cm. For example glass has a surface energy of around 300 dyne/cm and metals may have surface energies above 1000 dyne/cm. The skilled person will know that 1 dyne/cm is equivalent to 1 mN/m or 1 mJ/m$^2$, thus the term "dyne/cm" may be substituted by the term "mN/m" or the term "mJ/m$^2$".

The surface free energy of a particular surface may be determined with any method known in the art. For example the methodology by determining the Young contact angle θ with methods known in the art (see e.g. Jorda-Vilaplana et al., European Polymer Journal, Volume 58, September 2014, Pages 23-33) may be used.

For hanging in a target area, such as in a crop, the system for releasing beneficial mites according to the present invention may comprise hanging means. As the skilled person will readily understand, any means suitable for hanging such as a number of hooks or a number of threads may be used. Cardboard cards forming a hook are frequently used in the prior art systems for releasing beneficial mites such as the SWIRSKI-MITE range of products, including the SWIRSKI ULTI-MITE system of Koppert Biological Systems (Berkel and Rodenrijs, The Netherlands). Such cardboard hooks and similar hanging means are also suitable for use in the system for releasing beneficial mites of the present invention. Therefore, according to certain preferred embodiments the system for releasing beneficial mites comprises a hanging means comprising a planar material attached to the enclosing material The planar material preferably comprises openings suitable to function as a hook. It is preferred that the planar material of the hanging means serves as a covering for connections that connect the mite compartment with the space outside the mite compartment such that falling water does not fall directly onto the connections. For this it is preferred that the planar material has a width conforming to the width of a plane of the enclosing material where a connecting opening is located and is attached to the enclosing material such that its plane is at least essentially parallel to the plane of the enclosing material where said connecting opening is located, while covering said connecting opening.

The skilled person will understand that the system for releasing beneficial mites may also be introduced in a target area without a hanging means, for example by simply placing the system in the target area. As such the use of a hanging means is in no way required. In addition, systems for releasing beneficial mites without hanging means are valuable intermediate products that can easily be converted to systems including a hanging means. Also in this sense the systems without a hanging means are valuable contributions to the art.

According to some preferred embodiments it is preferred that in the area surrounding a connection, the outer surface comprises a material more hydrophobic than the selected water film maintaining material, such as a material having a Young contact angle of ≥61°, such as ≥65°, ≥70°, ≥75°, ≥80°, ≥85°, ≥90°, ≥100°, 150°. Most preferably the more hydrophobic materials is a hydrophobic material, viz. a material having a Young contact angle of ≥90°. The skilled person will know that the theoretical maximum of the contact angle is 180°. Thus according to the invention the contact angle of the more hydrophobic material preferably is between 61-180°. It is believed that the presence of a more hydrophobic material surrounding a connection may further reduce the chance of water entry from the outside surface into that connection. The area surrounding the connections referred to is an area up to a distance of 3 cm, such as up to 2.5 cm, such as up to 2.0 cm. such as up to 1.5 cm, such as up to 1.0 cm, such as up to 0.5 cm from the connection.

Further aspects of the invention relate to the use of the system according to the invention for introducing beneficial mites in a target area. The target area may be any area where the activity of the beneficial mites is desired. The beneficial mites may be predatory mites or mites suitable as a food source for predatory mites or for other predatory beneficial arthropods. As will be clear from the present description, in case the beneficial mites are selected from a predatory mite species, a mite species suitable as a food source for the predatory mites may also be present in the mite compartment of the system according to the invention. As will also be clear from the present description, in case the beneficial mites are selected from a mite species suitable as a food source for predatory mites or for other predatory arthropods, the predatory mites preferably are not present in the mite compartment of the system according to the invention. Or described differently, according to such embodiments, the population of beneficial mites preferably consists of a number of mite species suitable as a food source for predatory mites or for other predatory arthropods. For example in case the beneficial mites are predatory mites having a function in controlling crop pests, the target area may be a crop. The crop may be selected from, but is not restricted to (greenhouse) vegetable crops such as tomatoes (*Solanum lycopersicum*), peppers (*Capsicum annuum*), eggplants (*Solanum melogena*) Curcubits (*Cucurbitaceae*) such as cucumbers (*cucumis sativa*), melons (*Cucumis melo*) watermelons (*Citrullus lanatus*); soft fruit (such as strawberries (*Fragaria× annanassa*), raspberries (*Rubus ideaus*)), blueberries, (greenhouse) ornamental crops (such as roses, gerberas, chrysanthemums) or tree crops such as *Citrus* spp. Mites suitable as a food source for predatory mites or for other predatory arthropods having a function in controlling a crop pest may also be released in a crop in order to support the population development of predatory species present in the crop. The predatory mite may be a Mesostigmatid or Prostigmatid species as presented above. Other predatory arthropods may be selected form the family Miridae, such as *Macrolophus* spp., from the family Anthocoridae, such as *Orius* spp., for example *Orius laevigatus*, from the family Coccinellidae, such as *Adalia* spp. or *Cryptolaenmus montrouzieri*, from the Chrysopidae, such as *Chrysoperla* spp., for example *Chrysoperla carnea*.

According to alternative embodiments, the beneficial mites may have a function in controlling pests of an animal, the host animal, in particular pests of domestic animals, including farm animals and companion animals, such as poultry, cattle, horses, dogs or cats. According to such embodiments the target area may be a stable or sleeping area for the host animal. The system according to the invention may for example be used in support of the control of poultry red mite, by comprising as the beneficial mite a predatory mite selected from the genus *Hypoaspis*, such as *Hypoaspis angusta*, from the genus *Cheyletus*, such as *Cheyletus eruditis*, from the genus *Androlaelaps*, such as *Androlaelaps casalis*, from the family Laelapidae such as from the genus *Stratiolaelaps*, e.g. *Stratiolaelaps scinitus* (Womersley), *Gaeolaelaps*, e.g. *Gaeolaelaps aculeifer* (Canestrini), or from the genus *Macrocheles*, such as *Macrocheles robustulus* or an Astigmatid mite suitable as prey for a predatory mite from this selection. As the skilled person knows, these predatory mites have broader host ranges and thus may also be employed for controlling other pests. In addition other beneficial predatory arthropods may also be used to control pests of animal hosts. The system of the invention may also be used to release Astigmatid mites that may serve as a food source for such beneficial predatory arthropods and thus may support the survival and/or development of their populations, thus supporting the control of the pest of the animal host.

In yet other embodiments the beneficial mites are predators for pests of stored food products, such as stored product mites. In such embodiments the target area is a food product storage.

In the use of the invention the beneficial mite is introduced in the target area, by providing the system of the invention in the target area or in the proximity thereof. This may be done by placing the system of the invention in the target area or hanging it in the target area.

As is shown in the experiments below, the mite releasing system according to the invention maintains adequate functions when used in an environment wherein the ambient relative humidity (RH) is below 70%. This provides a system that is more robust and that may be employed under conditions where the RH fluctuates to values below 70% or even on average is below 70%. In view of the fact that environmental conditions may not always be controllable, the present invention provides a system with a reduced risk of failure due to too low ambient humidity. Therefore, according to certain preferred embodiments the system of the invention is for use in an environment wherein the ambient relative humidity (RH) may reach values below 65%, such as 65%-10%, or below 60%, below 55%, below 50%, below 45%, below 40%, below 30%, below 25%, below 20%, or below 15%. According to other preferred embodiments, the system of the invention is for use in an environment wherein the average ambient relative humidity (RH) is below 65%, such as 65%-10%, or below 60%, below 55%, below 50%, below 45%, below 40%, below 30%, below 25%, below 20%, or below 15%.

A further aspect of the invention relates to a method for controlling a pest susceptible of being preyed by a predatory mite species or other beneficial predatory arthropod species comprising providing the system according to the invention to a target area where the pest is to be controlled.

Yet a further aspect of the invention relates to a method for producing an agricultural product from a number of non-human organisms prone to infestation by a pest susceptible of being preyed by a predatory beneficial arthropod, said method comprising:
providing the number of non-human organisms in an area, the target area;
providing in or in the proximity of the target area a number of systems according to the invention;
providing to the number of non-human organisms suitable nutrients and environmental conditions to produce the agricultural product.

The number of non-human organisms may be selected from a crop species (as defined previously), an avian species, preferably a poultry species, such as chickens or turkeys, mammalian livestock.

A pest susceptible of being preyed by a predatory mite species should be understood as referring to a pest that is a suitable prey for a predatory mite present in the mite releasing system (the predatory mite selected as the beneficial mite).

A non-human organisms prone to infestation by a pest susceptible of being preyed by a predatory mite species should be understood as referring to a non-human organism that is prone to attract a pest, said pest being a suitable prey for a predatory mite present in the mite releasing system (the predatory mite selected as the beneficial mite). The non-human organisms prone to infestation by a pest thus is a suitable host for the pest and the pest is a suitable prey for the predatory mite present in the mite releasing system (the predatory mite selected as the beneficial mite).

Agricultural products that may be produced from a crop may include any plant material having agricultural value, such as plant biomass, seeds, fruits etcetera. Agricultural products that may be produced from an avian species such as poultry, in particular chickens or turkeys may include meat, eggs, feathers and manure. Agricultural products that may be produced from mammalian livestock, such as cattle, goats, sheep, pigs, may include meat and leather, milk, wool and manure.

The various embodiments of this aspect of the invention and the technical details connected thereto are similar to those of the use of the system for introducing beneficial mites in a target area as discussed above.

Yet a further aspect of the invention relates to a laminate comprising a metalized polymer film having a water vapour transmission rate of $\leq 5$, preferably $\leq 3.5$, more preferably 2.0 g/m$^2$*24 hours, and an outer layer of a fibrous material, preferably a layer of pressed plant fibres, more preferably pressed cellulose fibres, such as paper. As is already explained above, the skilled person will know that water vapour barrier materials are available that have an infinitely small water vapour transmissions rate. Thus the water vapour transmission rate of a selected metalized polymer film gas barrier material may be between 5.0 g/mm$^2$*24 hours and the theoretical value of 0.00 g/m$^2$*24 hours. Thus according to preferred embodiments, suitable metalized polymer film gas barrier materials may have a water vapour transmission rate between 5.0-0.01 g/m$^2$*24 hours, such as between 3.5-0.01 g/m$^2$*24 hours, between 3.5-0.5 g/m$^2$*24 hours, between 2.5-0.01 g/m$^2$*24 hours, between 2.5-0.5 g/m$^2$*24 hours, or between 2.0-0.5 g/m$^2$*24 hours. A value between 3.5-0.01 g/m$^2$*24 hours, such as 2.0 g/m$^2$*24 hours, is most preferred. As is clear from the above description of other aspects of the invention, the fibrous material should be capable of absorption of water i.e. it should be a water absorbing material. A laminate comprising such a combination of a metalized polymer film and an outer layer of such a fibrous material is not known in the art. In addition without any knowledge of the findings of the inventors of the present invention, it would not be obvious to produce such a laminate.

On the basis of his common general knowledge, the skilled person will be able to produce the laminate of the invention. In particular it is known in the art how to laminate polymer films with paper.

Further aspects of the invention relate to the use of the laminate of the invention as a construction material for a system for releasing beneficial mites and a method for producing a system for releasing beneficial mites. As will be clear from the above description of the other aspects of the invention, in said use the laminate is used such that the outer layer of fibrous material is at the exterior of the system. The method for producing a system for releasing beneficial mites comprises the step of:

providing a material, preferably a sheet material, the enclosing material, having a first surface, the inner surface, and a second surface, the outer surface, and comprising a gas barrier material having a water vapour transmission rate of ≤5, preferably ≤3.5, more preferably 2.0 g/m$^2$*24 hours, wherein the outer surface comprises a water film maintaining material;

constructing from the enclosing material a structure, such as a sachet, comprising a compartment suitable for holding beneficial mites, the mite compartment, wherein the structure is constructed such that the first surface is faced to the mite compartment;

placing a number of beneficial mites in the mite compartment.

The various steps of the use of the laminate and the method for producing a system for releasing beneficial mites must be understood in the context of the description relating to the other aspects of the invention. In view of this it must be understood that when the structure is constructed such that the first surface is faced to the mite compartment, the second surface is faced to the exterior of the mite releasing system. It will be further understood that the mite compartment will be provided with a number of openings connecting the interior of the mite compartment with the exterior. In addition it should be understood that the mite compartment should have a gas tight construction, i.e. it should have a water vapour transmission rate of ≤5 g/m$^2$*24 hours. As the skilled person will understand that is if no connecting opening to the exterior is present. Any seals or connections between different parts of enclosing material should be adapted to this.

The skilled person will understand that the step of placing a number of beneficial mites in the mite compartment may be performed at any suitable point in the production of the system for releasing beneficial mites, such as prior, during or after closing the mite compartment. In the current practice of producing mite releasing sachets, the exit openings are made after closing the mite compartment. Thus also according to the method of the present invention it is preferred that the number of openings connecting the interior of the mite compartment with the exterior are introduced (made) after closing the mite compartment.

The invention will now be further illustrated with reference to the attached figures and the example presented below. It should be emphasized that these figures, the description relating thereto and the example are only illustrative and by no means restrict the scope of the invention as defined in the claims.

FIG. 1 schematically shows a mite releasing system (1) according to an embodiment of the invention having the form of a stick shaped sachet. FIG. 1A presents a view on the front side of the mite releasing system (1) where the frontal panel (2) is located. FIG. 1B presents a view on the rear side of the mite releasing system (1) where a first rear panel (3) and a second rear panel (4) and the back of the sealing surface (5) are located. FIG. 1C presents a view in the direction of the longest axis of the elongated mite releasing system (1). The stick shaped sachet (1) is folded from a planar foil (BUI 43, Euroflex B. V., Zwolle, The Netherlands) shown in FIG. 1D with the exterior side facing upward. The parts forming the frontal panel (2) (35 mm wide and 85 mm long), the first rear panel (3), the second rear panel (4) and the sealing fin (5) in the folded conformation of the mite releasing system (1) are indicated. In addition in FIG. 1D a second sealing surface (6) that joins with sealing surface 5 and fold (7) are presented. In the folded and sealed conformation the fold (7) and the second seal surface (6) covered by seal surface (5) are not visible. The folded configuration presented in FIGS. 1A, 1B and 1C is obtained in a procedure similar to the procedures for producing sugar sticks and coffee creamer sticks using similar machines. For this sealing surface (5) is joined with sealing surface (6) and the parts are sealed at a suitable temperature above the sealing temperature of the material. A fold is then created along the line between parts (6) and (7) to allow the seal fin to bend back to the body of the stick. This allows the seal fin to be attached to the body of the stick on the second rear panel (4). Next the lower seal (8) is executed. This creates an open container that is filled with a mite composition comprising a mite population on a carrier. After filling, the upper seal (9) is executed. This upper seal (9) is broader than lower seal (8) in order to provide an attachment point for a hanging means, such as a cardboard hook (not shown). In FIG. 1D the locations of the lower seal (8) and upper seal (9) are presented with reference numbers in brackets, in view of the fact that in the planar unfolded situation the seals are not actually present.

Figure 2:
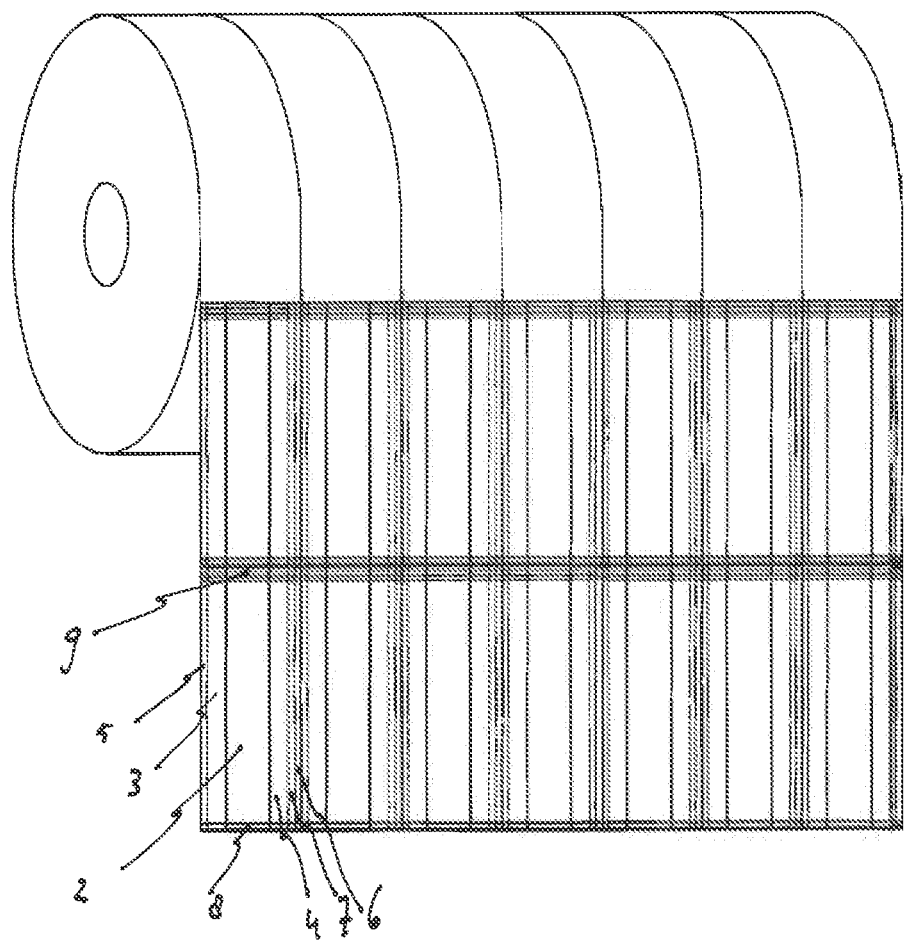
FIG. 2 shows how multiple mite releasing sachets can be formed from a roll of foil.

FIG. 2 shows how multiple mite releasing sachets can be formed from a roll of foil. For a single planar piece of foil the parts forming the frontal panel (2), the first rear panel (3), the second rear panel (4) and the sealing fin (5) in the folded conformation of the mite releasing system are indicated. In addition inside fin flap (7), part (6) covered by the fin seal and the parts where heat seals (8) and (9) will be positioned are indicated. Cutting, folding, sealing, filling with a mite composition comprising a mite population in association with a carrier, and introduction of the opening (10) to connect the mite compartment with the space outside the mite compartment may be performed fully automated with technology and procedures similar to the technology and procedures used for producing sugar sticks and coffee creamer sticks.

EXPERIMENTS

Experiment 1

Mite Cultures

A stock rearing of *Amblyseius swirskii* on the prey mite *Carpoglyphus lactis* on a carrier material of humidified bran (20% w/w water content). Nutrients for *C. lactis* were provided by the farinaceous material of the bran and 5% (w/w) yeast extract added to the bran. The number of mites in the rearing mixture was assessed using standard counting methods as disclosed in van Lenteren, J. C., Hale, A., Klapwijk, J. N., van Schelt, J. and S. Steinberg (2003) Guidelines for quality control of commercially produced natural enemies. In: van Lenteren, J. C. (ed) Quality control and production of biological control agents: Theory and testing procedures CABI Publishing, Wallingford UK, pp 293-294.

Procedure

Mite releasing systems (sachets) having the following design variations of the mite compartment were compared:
1. Polyethylene (PE) coated paper (Kraft paper 40 g/m² laminated with extruded PE 17 g/m² (KBM 40+17 gr) Burgo, Italy), standard* form of the mite compartment and a single opening with a diameter of 0.65±0.05 mm connecting to the space outside the mite compartment.
2. PE coated paper (Kraft paper 40 g/m² laminated with extruded PE 17 g/m² (KBM 40+17 gr) Burgo, Italy), standard* form of the mite compartment and a single opening with a diameter of 1.3 mm connecting to the space outside the mite compartment.
3. BUI43 foil (Euroflex B. V., Zwolle, The Netherlands), standard* form of the mite compartment and a single opening with a diameter of 0.65±0.05 mm connecting to the space outside the mite compartment.
4. BUI 43 foil (Euroflex B. V., Zwolle, The Netherlands), standard* form of the mite compartment and a single opening with a diameter of 1.3 mm connecting to the space outside the mite compartment.
5. BUI 43 foil (Euroflex B. V., Zwolle, The Netherlands), stick** form (stick shape) of the mite compartment and a single opening with a diameter of 0.65±0.05 mm connecting to the space outside the mite compartment.

*Standard form is as used in standard mite release system (sachet) of Koppert Biological Systems (Berkel en Rodenrijs, the Netherlands) used at present in the SWIRSKI-MITE PLUS, products (mite compartment size excluding the seal strips: 50×50 mm). On the basis of these dimensions, the volume of the material filled (2.3 grams of a carrier material corresponding to about 11.5 cc) and the head space maintained, the volume of the interior of the mite compartment (x) was determined to be about 14 cc.

**Stick form is alternative shape according to certain embodiments of the invention (mite compartment size excluding the seal strips: 35×65 mm). On the basis of these dimensions, the volume of the material filled (2.3 grams of a carrier material corresponding to about 11.5 cc) and the head space maintained, the volume of the interior of the mite compartment (x) was determined to be about 14 cc.

The BUI sachets were made manually with a hand-sealing machine and the PE paper sachets were produced in the production facilities of Koppert B. V. according to the specifications for the SWIRSKI-MITE PLUS product. Near the top end of the sachets a single opening with the diameter of 0.65±0.05 mm ($y=\pi*(0.65/2)^2=0.33$ mm²) or with a diameter of 1.3 mm ($y=\pi*(1.3/2)^2=1.3$ mm²) was made with two different types of needles having shafts with diameters of the indicated sizes. Both the 0.65 and the 1.3 mm diameter opening are relatively small in respect of what is used in the prior art.

Mite countings according to standard methods (van Lenteren et al., 2003 supra) carried out on the carrier material of humidified bran and nutrients revealed that it contained approx. 112 *A. swirskii* and 277 *C. lactis* per gram at the beginning of the experiment. 2.3 grams (about 11.5 cc) of the carrier material were filled into the sachets (resulting in approx. 257 *A. swirskii* and approx. 637 *C. lactis* per sachet). Thereafter the sachets were sealed. In this way 45 sachets of each type were prepared.

36 sachets of each type were hung alternately on a cotton thread using paperclips in a climate cabinet regulated at 22 degrees Celsius and a relative humidity of 50%. Twice a week, 3 sachets of each type were sampled in the following manner. The sachets were opened and the content of the 3 sachets of the same type was mixed and the number of mites in the mixture was assessed using standard counting methods (van Lenteren et al., 2003 supra). At the same time the water activity (Rotronic HP23-AW-A with HC2-AW) and the moisture content (Sartorius MA150) of the carrier material were measured. This procedure was repeated until the number of mites in the sachets decreased significantly.

At the same time the other sachets were used for a walking out test.

From each type, 3 sachets were placed together into a glass jar. Each glass jar was placed separately in a plastic bucket (10 liters) in a layer (2 cm deep) of water to which some drops of soap was added. Buckets were placed into another climate cabinet also regulated at 22 degrees Celsius and a relative humidity of 50%. Mites (predatory mites an prey mites) escaping the jars we captured in the soapy water solution. Twice a week all glass jars were transferred to new, clean, plastic buckets with new soapy water solution. This procedure was repeated until escape (production) of mites decreased significantly. The mites in the soapy water solution were counted.

Results

Figure 3A:
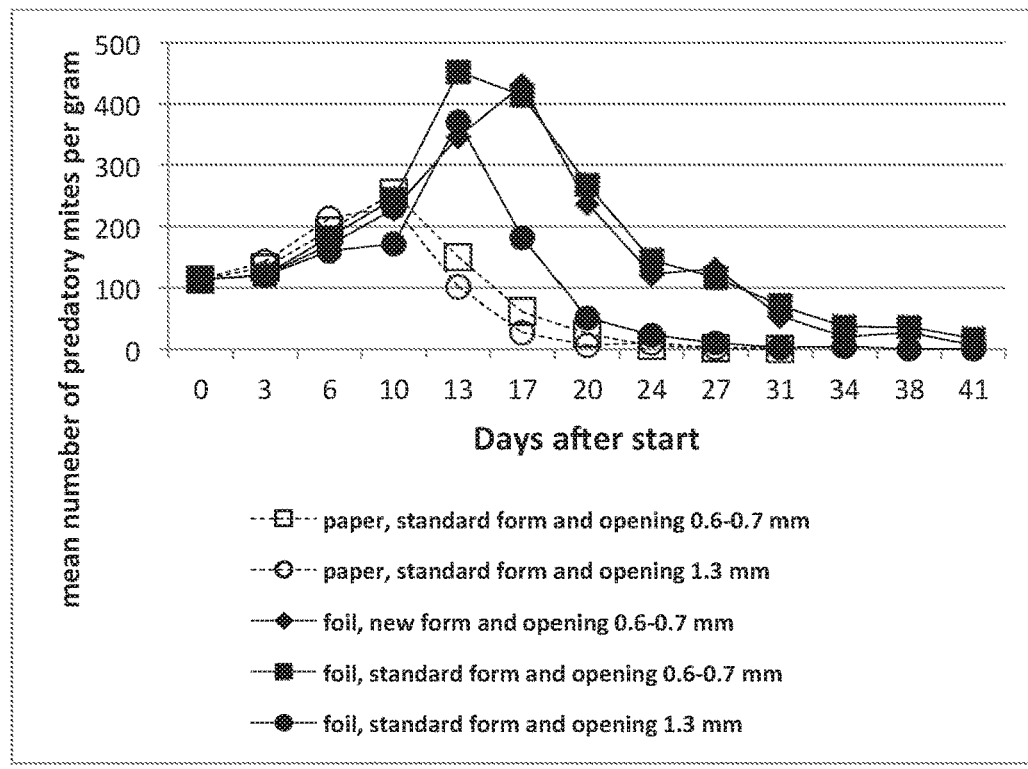
FIGS. 3A and 3B show the results of countings of predatory mites (*A. swirskii*) and prey mites (*C. lactis*) inside a mite releasing systems of the non-prepublished patent applications EP17151679.2 and PCT/NL2017/050022 (now published as EP3192366A1 and WO2017/123094 A1 respectively) having a gas barrier material enclosing the mite compartment. The countings relate to the different design variations as tested in the experiment of these non-prepublished applications. This experiment is also presented in the present application as experiment 1 for reference to the effect of the gas barrier material.
Figure 3B:
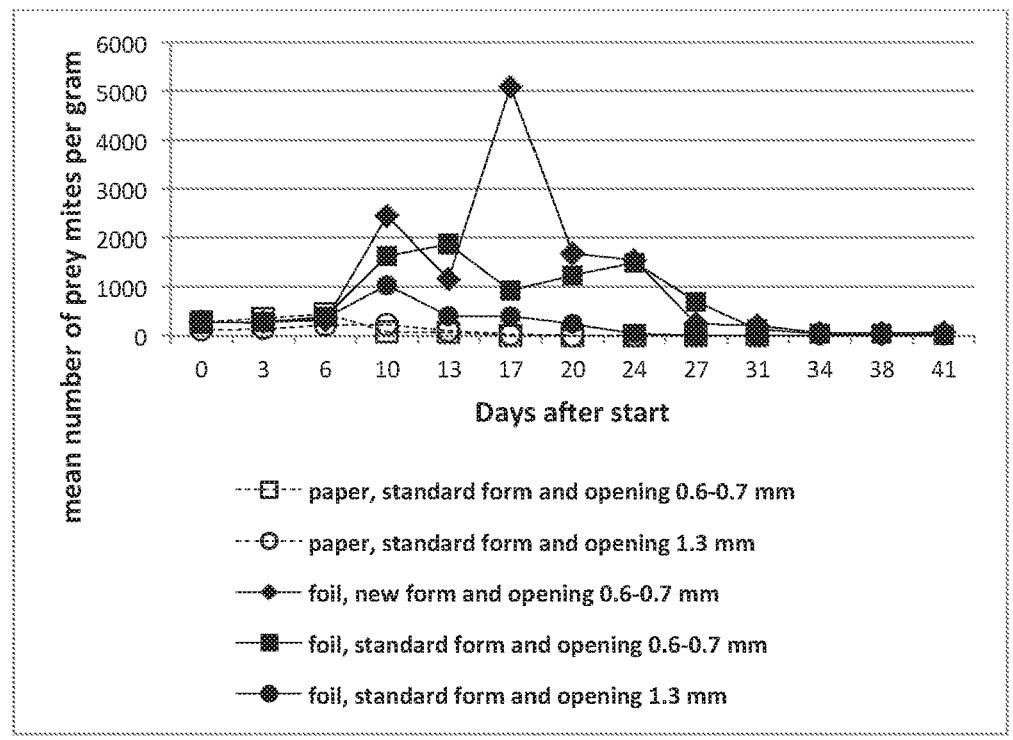
Figure 4A:
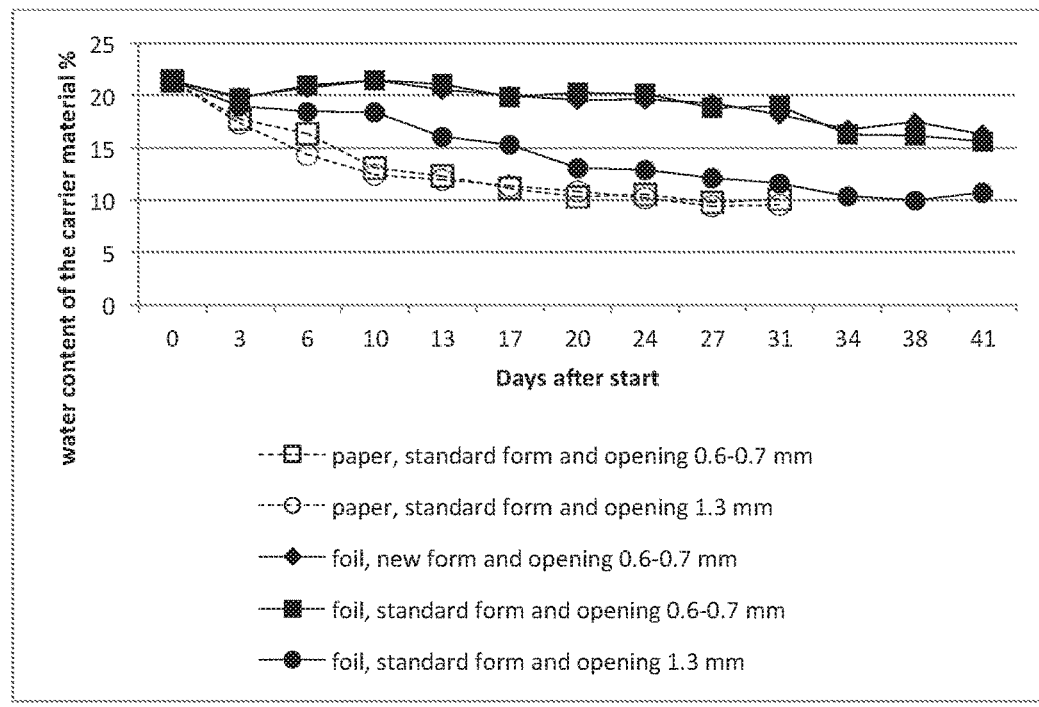
FIGS. 4A and 4B show the values of the water activity ($a_w$) and water content over time inside the mite releasing systems of the non-prepublished patent applications EP17151679.2 and PCT/NL2017/050022 (now published as EP3192366A1 and WO2017/123094 A1 respectively).
Figure 4B:
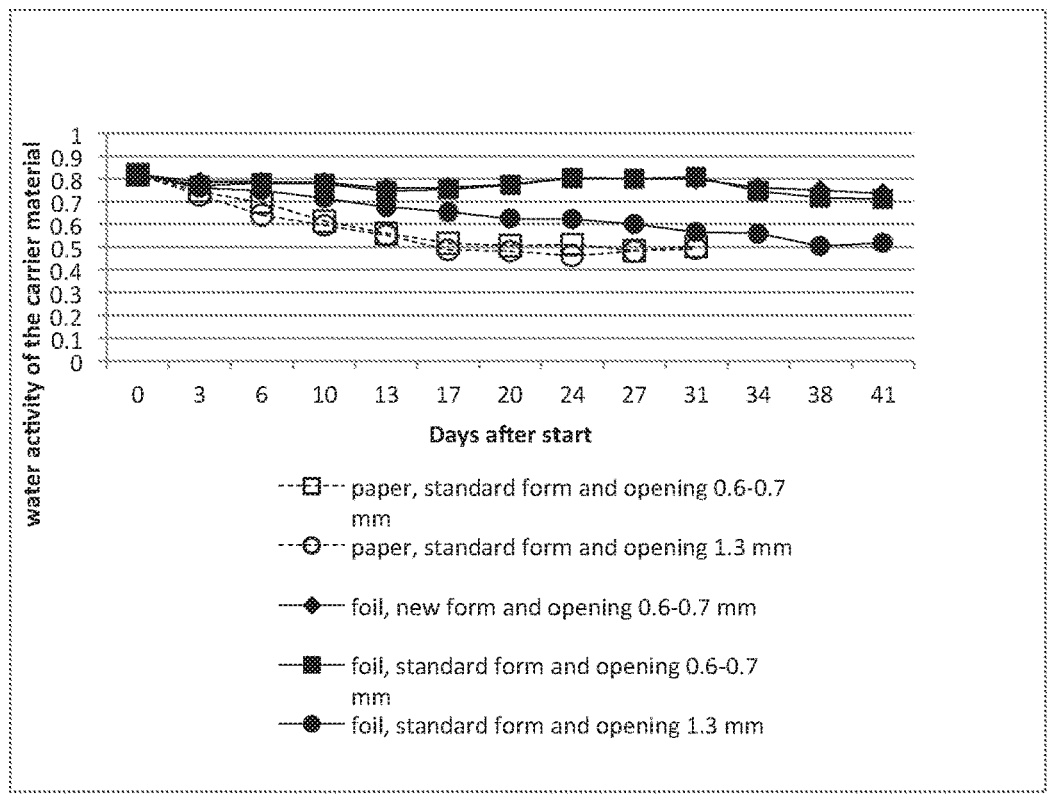
Figure 5A:
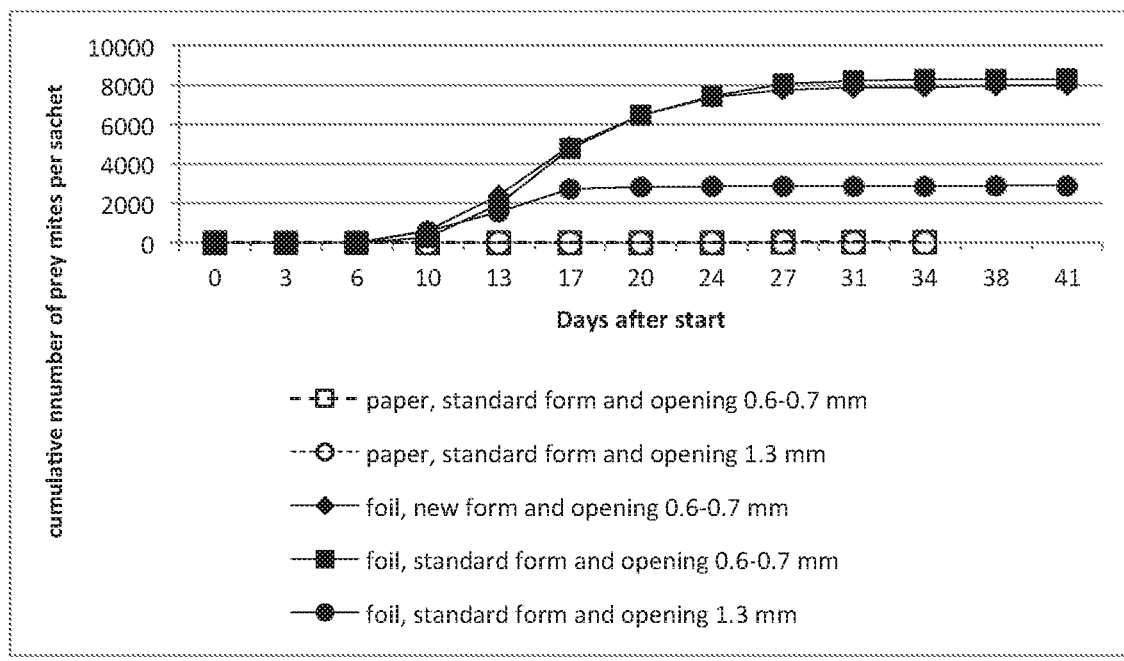
FIGS. 5A and 5B show the results of countings of predatory mites (*A. swirskii*) and prey mites (*C. lactis*) collected in a walking out test as tested in experiment 1 relating to the mite releasing systems of the non-prepublished patent applications EP17151679.2 and PCT/NL2017/050022 (now published as EP3192366A1 and WO2017/123094 A1 respectively).
Figure 5B:
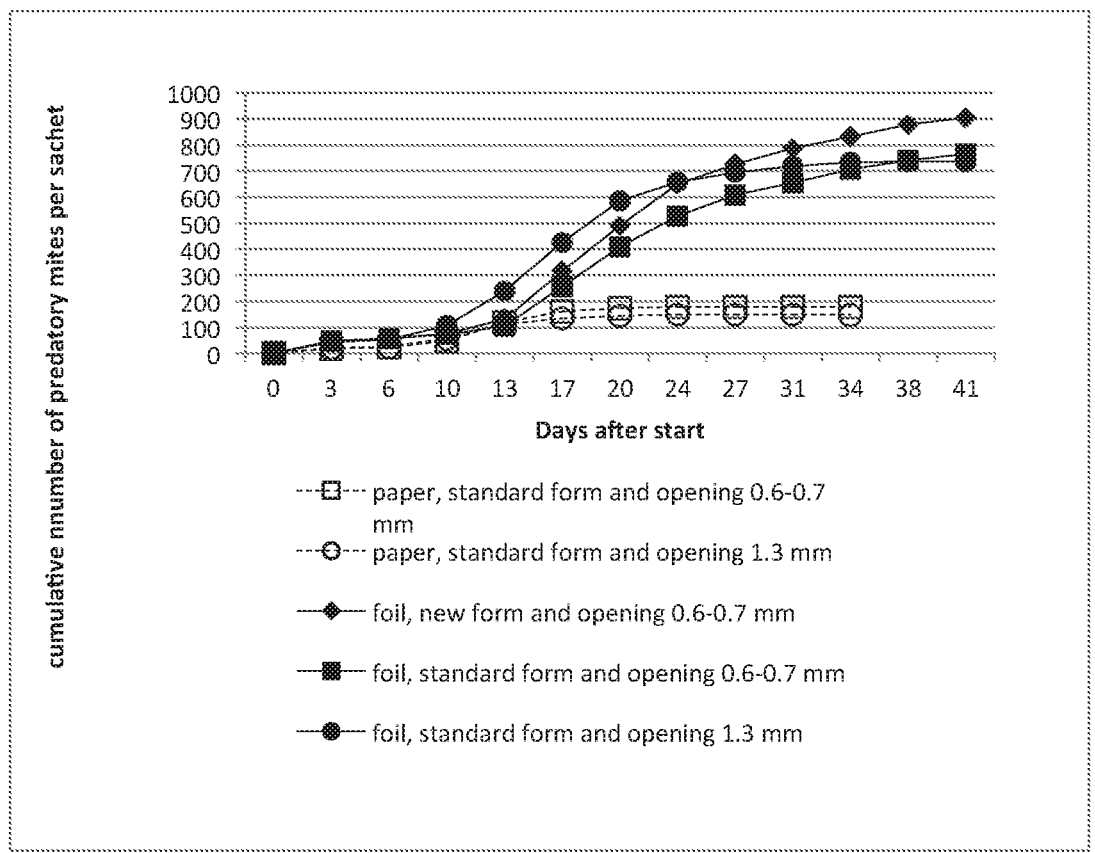
Figure 6:
FIG. 6 shows sachets used in experiment 2 in front view. From left to right treatments (C), (D), (A), (B). Treatments (C) and (D) are according to the invention.
Figure 7:
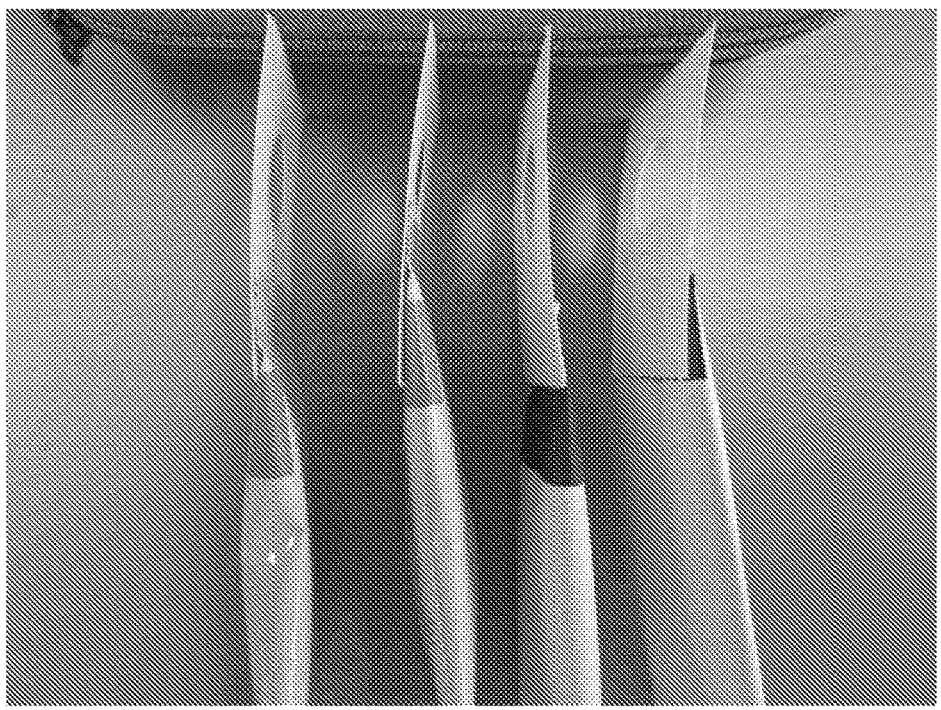
FIG. 7 shows sachets used in experiment 2 in side view. From left to right treatments (A), (B), (C), (D).

The results of countings of predatory mites (*A. swirskii*) and prey mites (*C. lactis*) inside the mite releasing systems having the different design variations are shown in FIGS. 3A and 3B. FIGS. 4A and 4B show the values of the water activity ($a_w$) and moisture content over time inside the mite releasing systems having the different design variations. FIGS. 5A and 5B show the results of countings of predatory mites (*A. swirskii*) and prey mites (*C. lactis*) collected in the soapy water used in the walking out test. These numbers represent the number of mites that actively dispersed out the mite releasing systems during the experiment.

CONCLUSIONS

On the basis of the data presented it can be surprisingly concluded that mite populations can be maintained over prolonged periods in mite releasing systems constructed from materials having a low water vapor transmission rate (and an associated low transfer rate for one or more metabolic gasses) while having only a small opening for gas exchange. More surprisingly, mite population development inside such systems is improved under conditions of 50% RH in comparison to prior art mite releasing systems. Such conditions and lower RH conditions are often encountered in many agricultural settings, in particular in growing outdoor crops (there is at least a risk of these conditions occurring). Thus mite releasing systems according to the invention are better adapted to variations in humidity conditions then prior art mite releasing systems and therefore may be used with less risk of failure in situations where there is a risk of low RH conditions (below 65% or lower, such as below 55%). Furthermore, it is also surprising that mite dispersal out of the mite releasing systems is increased with a decreasing size of the opening connecting the mite compartment and the space outside the mite compartment.

Experiment 2

Materials

Two hundred sachets (34 mm*84 mm w*h) were made for this experiment. All sachets where filled with the standard content of Swirski-mite plus sachets (*Amblyseius swirskii* with *Carpoglyphus lactis* in bran as carrier) 100 sachets were made with 34 g/$m^2$ BUI43 foil (Euroflex B. V., Zwolle, The Netherlands) and 100 sachets with 34 g/$m^2$ BUI43 foil with 40 g/$m^2$ kraft paper on the outer side of the sachets. The BUI43 foil+kraft paper was custom made by Euroflex B.V on request from Koppert B. V. by laminating kraft paper of 40 g/$m^2$ weight on the transparent cellulose film layer of the BUI43 foil. Standard procedures for laminating paper sheets on polymer films were used in this lamination process. The sachets were machine produced analogous to the production of ULTI-MITE SWIRSKI sachets (Koppert B. V., Berkel and Rodenrijs, The Netherlands) without an exit hole and hanging card. After machine production of the sachets, exit holes were manually made by burning a 0.6-0.7 mm diameter hole with a hot needle approximately 2 cm below the top of the sachet on the front side of the sachet (back side containing the vertical seal). To rule out water entry via the seals, the top and bottom seal of each sachet was dipped (~2 mm) in hot melt glue. Finally a hanging card serving as hook was glued onto each sachet. On 50 sachets with BUI foil and 50 sachets with BUI foil+kraft paper the hanging card was placed on top of the sachet, only covering the seal strip. On the other 50 sachets of each type of sachets the sachet was glued higher on the hanging card resulting in the hanging card covering the exit hole in the sachet. Table II shows an overview of the treatments and FIGS. 6 and 7 show sachets of each treatment.

TABLE II overview of experimental treatments.

| Treatment | Foil type | Remarks |
|---|---|---|
| A. | 34 g/$m^2$ BUI43 foil | Exit hole not covered |
| B. | 34 g/$m^2$ BUI43 foil | Exit hole covered by hanging card |
| C. | 34 g/$m^2$ BUI foil + 40 g/$m^2$ kraft paper | Exit hole not covered |
| D. | 34 g/$m^2$ BUI foil + 40 g/$m^2$ kraft paper | Exit hole covered by hanging card |

Method

Directly after the 200 sachets were made the sachets were hung in the glasshouse at Koppert's facilities on Jun. 22, 2017. The sachets where hung on horizontally placed bamboo sticks approximately 15 cm above the floor in 2 blocks of 50*50 cm each. The treatments were randomly distributed. A sprinkler (Revaho, type DAN-8991, green, 105 l/h) was placed approximately 60 cm above the floor in the middle of the sachets to provide a homogenous spray of water on the sachets. During 14 days water was sprinkled 4 times a day (8:10, 9:40, 13:45 & 15:40h) each time for a period of 90 seconds. The amount of water sprinkled in a 90 s period was about 1020 g/$m^2$. The water applied was irrigation water (EC 2.0 & pH 5.5) having the composition presented in FIG. 8. Temperature and relative humidity was measured 3 meters away from the experiment, mean temperature during the experiment was 23.1° C. and mean RH was 63.0%.

After 14 days of exposure to the 4 short rain showers per day all sachets were collected and the content of each sachet was evaluated and rated according to a 4 point scale. 1.) the bran is dry (evaluated on the basis of the bran being loose and non-clumping), 2.) the brain is slightly moist (evaluated on the basis of the bran showing some clumping, but without a visible wetness), 3.) a part of the bran is visibly wet, the wet area is less than 20% of the volume, 4.) more than 20% of the volume of the bran is visibly wet.

Results

FIG. 9 shows the percentage of sachets scored according to the 4 point rating scale for the different treatments (A, B, C, D). The results clearly show that the proportion of sachets having a dry bran content (rating 1) is higher for the sachets having a paper outer layer (treatments C, D), in comparison to the treatments where the outer layer was from the BUI34 laminate foil (treatments A, B). Also, the proportion of sachets having visibly wet bran (ratings 3 and 4) was clearly decreased for the sachets having a paper outer layer (treatments C, D), in comparison to the treatments where the outer layer was from the BUI34 laminate foil (treatments A, B). Surprisingly, covering the exit hole with the hanging card in treatment (B) decreased the proportion of sachets having a dry bran content (rating 1) in comparison to treatment (A). This is not an artefact and was also observed in previous tests. Contrary to this, in treatment (D), also having a covered exit hole, the proportion of sachets having a dry bran content (rating 1) was on the same level and even somewhat increased relative to treatment (C). Treatment (D) did not result in any sachets having more than 20% wet bran (rating 4) whereas sachets constructed according to treatment (A) had a significant proportion of such sachets having wet bran.

DISCUSSION

The trend of an increase in the number of sachets having a dry content (rating 1) and the decrease of sachets having a visibly wet content (ratings 3 and 4) between treatment groups (A) and (B) on the one hand and (C) and (D) on the other hand, clearly shows that the provision of a porous water absorbing layer (the paper layer) on the outer surface of a system for distributing mites results in an improved control of undesired water inflow from the exterior of the system to the mite compartment. Thus increasing the chance of maintain under wet conditions suitable conditions in the mite compartment for development of the mite populations. The combination of a porous water absorbing layer with the exit hole covered (treatment (D)) had the best results in reducing the risk of water inflow.

On the basis of these results and in view of the above mentioned theory concerning the mode of action of the porous water absorbing paper layer on the exterior of the mite releasing system, it is justified to expect that surfaces having good wetting properties for water will also have beneficial effects in reducing the risk of water entry into the mite compartment. Thus it may be expected that other surfaces having good wetting properties for water will increasing the chance of maintain under wet conditions suitable conditions in the mite compartment for development of the mite populations.

It should be noted that for current mite distribution systems, it is advised not to expose them to direct rain and/or irrigation water. The current invention therefore is a mayor advancement in the development of a mite releasing system which has a good performance under exposure to direct rain and/or irrigation water.

Experiment 3

Background

This experiment was performed to investigate the exterior water flow pattern on the surface of alternative water film maintaining materials, in comparison to the paper laminated BUI34 material used in experiment 2. The materials investigated were first characterized in respect of their Your contact angle with water. Water film maintaining capacity of the materials performing similar to the paper laminated BUI34 material in the water runoff experiment was confirmed in a water film maintenance experiment.

Materials & Methods

A variety of materials used as packaging materials was tested (see table III). To provide a surface treated with a hydrophilic coating, BUI34 was treated with a hydrophilic NanoPro Titaniumdioxide ($TiO_2$) coating from Clean-TechNoord. This is a high performance titanium dioxide photocatalytic sol manufactured according to the Nanohydrosynthetic process. The coating was applied according to the instructions of the supplier.

Contact Angle Measurement:

Materials were taped to a stiff plate such that the material formed a flat plane and the material was slightly tensed. These plates were placed on an elevated table. A 20 µl droplet of the irrigation water used in experiment 2 was carefully applied on the material with a P20 Gilson pipet. Each droplet was photographed with a fixed Cannon 5D mark 4 camera and a 100 mm F2.8 macro lens. Materials we preincubated at 20 degrees Celsius and 77% relative humidity and the test was performed under the same conditions. The focus points in each photograph were the left and right side of the droplet end. Each picture was then imported into Inkscape 0.91 where they were rotated such that the base of the droplet formed a horizontal plane. After that, tangent lines were drawn from the base of the droplet in accordance with contact angle measuring theory. The angle between the horizontal plane and the tangent line was measured with the built in measuring tool.

Water Runoff:

An experimental set-up was created to determine the runoff behavior. In this set-up selected materials were fixed to a stiff plate and placed vertically. A mist spray was used to spray small water droplets on the materials from a 30 cm distance. The number of sprays required to have the first droplet run off the bottom of the vertically positioned material was recorded. A single spray had an average weight of 0.175 gram (determined by averaging the combined weight of 10 sprays: n=11, 0.194 std). The water used was the irrigation used in experiment 2. Materials we preincubated at 20 degrees Celsius and 77% relative humidity and the test was performed under the same conditions.

Water Film Maintenance:

By using a P2000 Gilson pipet, 1 ml of water (the irrigation used in experiment 2) was applied on several materials, such that the water formed a single cohesive water bead. With a single swipe, a glass stirring rod was pulled through the water mass. Each swipe was equal in length. Photographs of the water mass were taken before and after the swipe and the pattern difference were evaluated.

Results

Contact Angle:

The contact angles of the tested materials are listed in table III. The measured value for PLA corresponds to reported values (see for example Jorda-Vilaplana et al., European Polymer Journal, Volume 58, September 2014, Pages 23-33). For the microscope slide glass used there is a discrepancy between the contact angle value determined for the specimen used and the reported value for glass. The values determined in this test for the microscope slide specimen used are considered accurate, in view of the performance of this glass specimen in the other tests. Possibly the microscope slide glass used has received a treatment influencing the wetting properties.

TABLE III

| | Contact angle | | | | |
|---|---|---|---|---|---|
| Material | avg-L | avg-R | avg-L/R | std | n (L + R) |
| Water saturated 34 g/m² BUI foil + 40 g/m² kraft paper | 3.0 | 3.0 | 3.0 | 0.0 | 2.0 |
| Microscope slide glass | 12.0 | 11.0 | 11.5 | 4.1 | 4.0 |
| 34 g/m² BUI foil + TiO2 nano-coating | 34.5 | 33.2 | 33.9 | 8.3 | 22.0 |
| Ref. nr. 1213 PLA 25 my | 75.0 | 72.5 | 73.8 | 2.5 | 4.0 |
| 34 g/m² BUI foil | 74.6 | 75.4 | 75.0 | 4.0 | 20.0 |
| Ref. nr. 2603 - PE (25 my) | 95.0 | 95.6 | 95.3 | 6.4 | 10.0 |
| Ref. nr. 1214 - Bio 01 (25 my, wit) | 103.4 | 102.8 | 103.1 | 3.3 | 10.0 |

Figure 10:
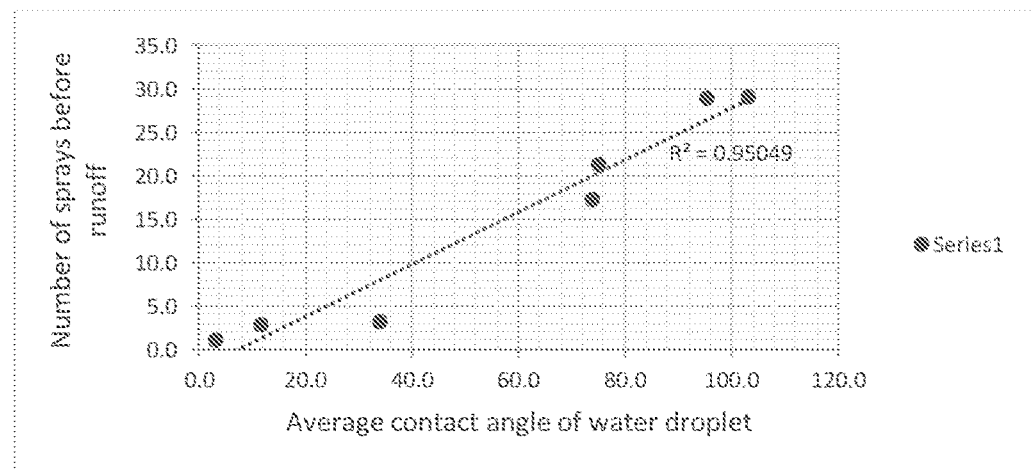
FIG. 10 presents a graphical representation of the data of table IV.

Water Runoff:

The results of the water runoff test are presented in table IV below and in FIG. 10. The results clearly show that materials having a small contact angle with water, required the fewest number of sprays before a droplet formed and ran of the material. The number of sprays required to achieve the same affect increased with the contact angle. Hydrophobic materials, with a contact angle larger than 90 degrees required most sprays. It may further be noted that dry 34 g/m² BUI foil+40 g/m² kraft paper required an average of 11.2 sprays (std.=0.8, n=6.0) for the first droplet to run off the bottom of the vertically positioned material. For the water saturated 34 g/m² BUI foil+40 g/m² kraft paper, the microscope slide glass, and 34 g/m² BUI foil+TiO2 nano-coating it was observed that droplet movement was associated with a water film trace.

TABLE IV

| | Contact | Water runoff | | |
|---|---|---|---|---|
| Material | angle avg-L/R | avg nr. spray | std | n |
| Water saturated 34g/m² BUI foil + 40 g/m² kraft paper | 3.0 | 1.0 | 0.0 | 6.0 |
| Microscope slide glass | 11.5 | 2.8 | 0.5 | 4.0 |
| 34 g/m² BUI foil + TiO2 nano-coating | 33.9 | 3.1 | 1.3 | 9.0 |
| Ref. nr. 1213 PLA 25 my | 73.8 | 17.2 | 4.3 | 5.0 |
| 34 g/m² BUI foil | 75.0 | 21.2 | 7.3 | 9.0 |
| Ref. nr. 2603 - PE (25 my) | 95.3 | 28.9 | 4.4 | 7.0 |
| Ref. nr. 1214 - Bio 01 (25 my, wit) | 103.1 | 29.0 | 3.0 | 6.0 |

The results clearly show that more water remains on surfaces having larger Young contact angles for water and that water runs off more easily from surfaces having smaller Young contact angles for water. The results also show that the 34 g/m² BUI foil+TiO₂ nano-coating and microscope slide glass are comparable to 34 g/m² BUI foil+40 g/m² kraft paper, in respect of how water runs off.

Figure 11A:
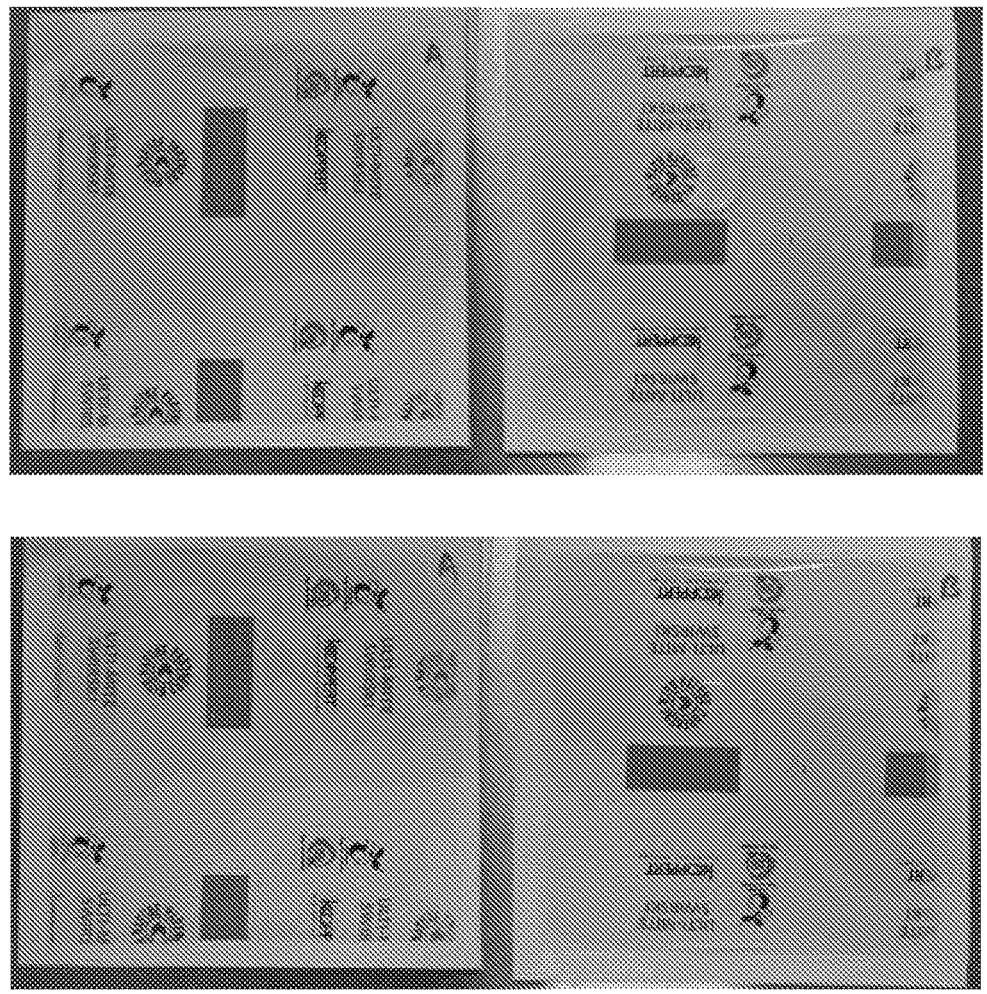
FIGS. 11A-11C show pictures of the waterfilm experiment of experiment 3.
Figure 11B:
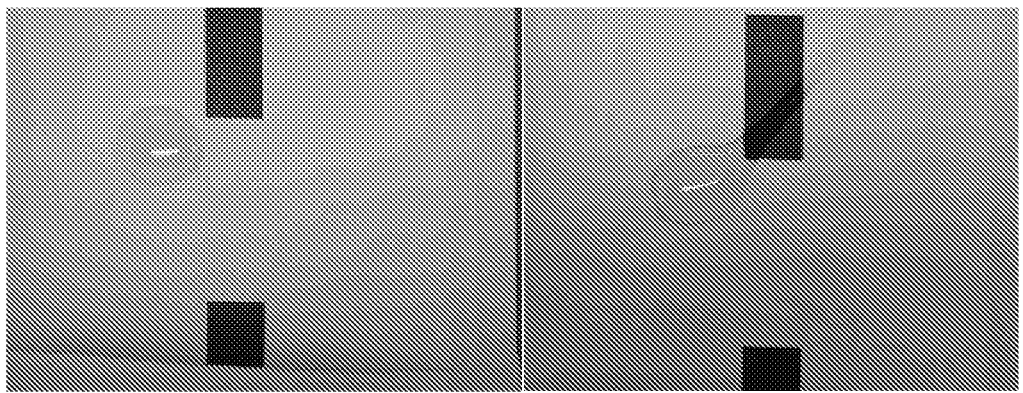
Figure 11B:
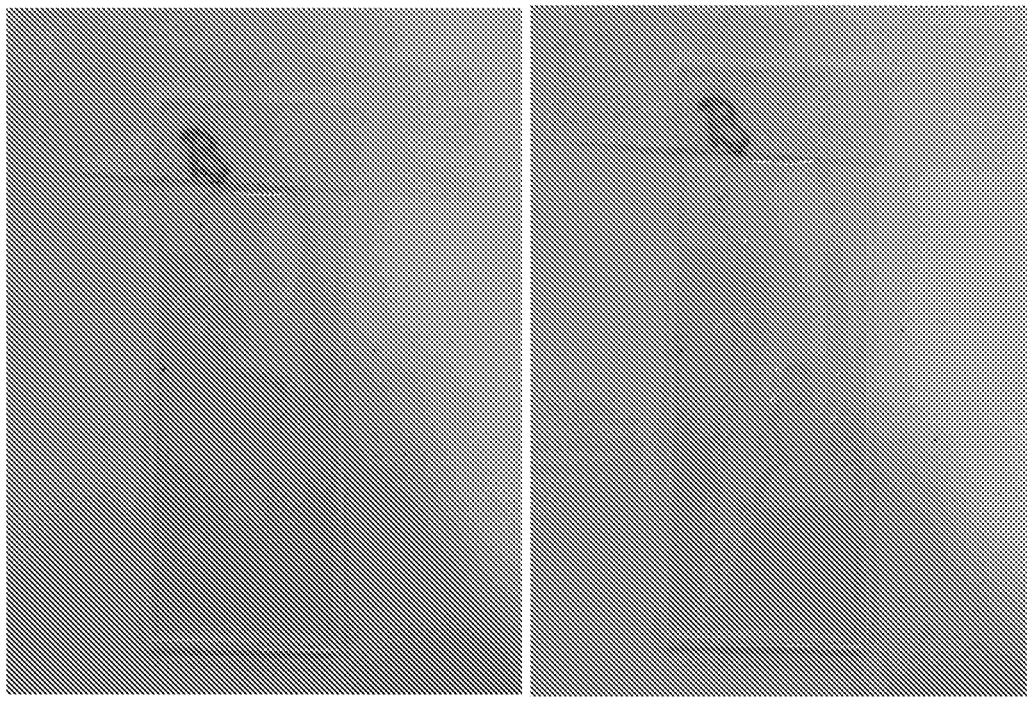
Figure 11C:
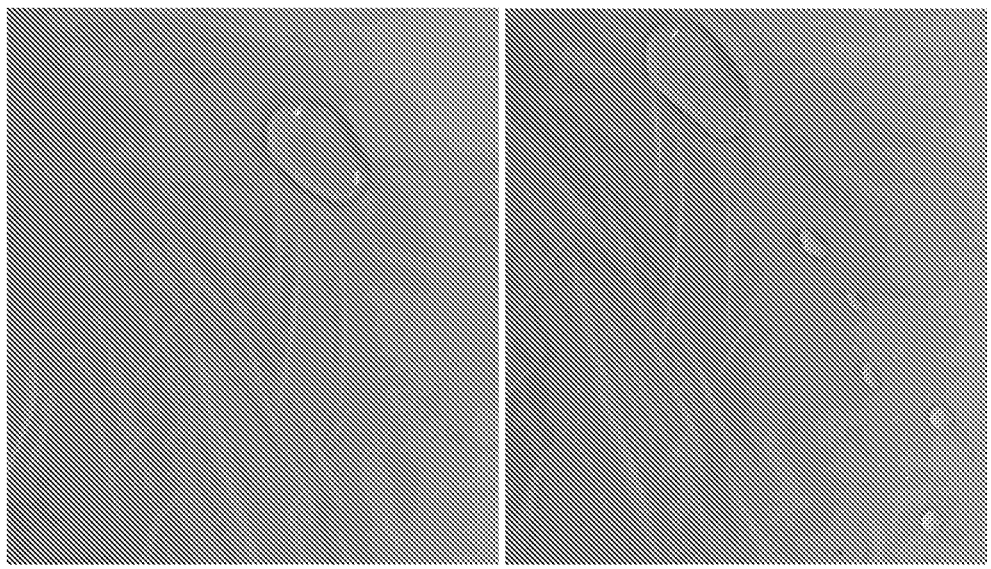

Water Film:

The 34 g/m² BUI foil has a larger surface angle than the 34 g/m² BUI foil with TiO₂ nano-coating (contact angles respectively 75 and 33.9 degrees). When the glass rod was swiped through the water bead on the TiO₂ coated 34 g/m² BUI foil, a water film was left behind, marking the path of the swipe. On the uncoated 34 g/m² BUI foil two separate water beads were left behind with no visible water film marking the path of the swipe. The result from the droplet on the microscope slide glass was comparable to that of the TiO₂ coated BUI foil, while Ref 1214 Bio 01 was more in line with that of the untreated BUI foil. Also the dry 34 g/m² BUI foil+40 g/m² kraft paper was able to maintain a water film after disruption of the water bead with the glass rod. Pictures are presented in FIGS. 11A-11C. In particular for the TiO₂ coated BUI foil and the microscope slide glass no clear water bead/drop is visible, this is because a water film was strongly maintained.

The results clearly confirm that a small Young contact angle with water correlates with the ability of a material to maintain a water film at its surface. From the tested materials, the 34 g/m² BUI foil+40 g/m² kraft paper, the microscope slide glass and the TiO₂ coated BUI foil can be grouped as materials that can maintain a water film.

The invention claimed is:

1. A system for releasing beneficial mites comprising a mite compartment holding a population of a beneficial mite species and a food source for the beneficial mites wherein said mite compartment is enclosed by an enclosing material having an inner surface bordering the mite compartment, an outer surface at the exterior of the mite compartment and comprising a gas barrier material having a water vapour transmission rate of ≤5 g/m²*24 hours, said mite compartment having a volume of x mm³, wherein x is between $3*10^3$ and $600*10^3$ mm³ and wherein the system further comprises a number of connections that connect the mite compartment with the space outside the mite compartment, said number of connections each having an area y, wherein y is between 0.1 and 4.0 mm², wherein the sum of the areas of the number of connections is Σy and wherein $5*10^3$ mm≤x/Σy≤$70*10^3$ mm, wherein the outer surface of the enclosing material comprises a water film maintaining material.

2. The system according to claim 1, wherein the gas barrier material comprises a polymer-metal laminate.

3. The system according to claim 1, wherein the enclosing material is a laminate comprising the gas barrier material and the water-film maintaining material is a water absorbing porous material.

4. The system according to claim 1, wherein the outer surface is selected such that water has a Young contact angle θ of at most 60°, such as ≤60°, ≤55°, ≤50°, ≤45°, ≤40°, ≤35°, ≤30°, ≤35°, ≤30°, ≤25°, ≤20°, ≤15°, ≤10°, ≤5°.

5. The system according to claim 1, wherein the water-film supporting material is a material having a surface energy of at least 43 dyne/cm, such as ≥43, ≥44, ≥45, ≥50, ≥55, ≥60, ≥65, ≥70, ≥75 dyne/cm.

6. The system according to claim 1, wherein the beneficial mite species is a predatory mite species.

7. The system according to claim 1, wherein the beneficial mite species is a mite species from the suborder Astigmata.

8. The system according to claim 1, wherein the beneficial mite species is a predatory mite species and the food source for the predatory mite species comprises a prey mite species selected from the suborder Astigmata.

9. The system of claim 2, wherein the polymer-metal laminate is a polymer-metal laminate film.

10. The system of claim 2, wherein the polymer-metal laminate comprises a metalized polymer film.

11. The system of claim 3, wherein the water absorbing porous material is a porous fibrous material.

12. The system of claim 3, wherein the water absorbing porous material is a porous material comprising pressed plant fibers.

13. The system according to claim 1, wherein the beneficial mite species is a predatory mite species selected from: Mesostigmatid mite species and Prostigmatid mite species.

14. The system according to claim 1, wherein the beneficial mite species is a predatory mite species selected from:
    i) Phytoseiidae;
    ii) Ascidae;
    iii) Laelapidae;
    iv) Macrochelidae;
    v) Parasitidae;
    vi) Tydeidae;
    vii) Cheyletidae;
    viii) Cunaxidae;
    ix) Erythraeidae;
    x) Stigmaeidae; and
    xi) Anystidae.

15. The system according to claim 7, wherein the beneficial mite species from the suborder Astigmata is selected from:
    i) Carpoglyphidae;
    ii) Pyroglyphidae;
    iii) Glycyphagidae;
    iv) Acaridae; and
    v) Suidasiidae.

16. The system according to claim 1, wherein the population of the beneficial mite species is in association with a carrier.

* * * * *